United States Patent [19]

Brugge et al.

[11] Patent Number: 5,981,262
[45] Date of Patent: Nov. 9, 1999

[54] HUMAN SYK

[75] Inventors: Joan Brugge, Concord; Jay Morganstern, Boston; Lily Shiue; Lynne Zydowsky, both of Cambridge; Mark Zoller, Weston, all of Mass.; Anthony Pawson, Toronto, Canada

[73] Assignee: Ariad Pharmaceuticals, Inc., Cambridge, Mass.

[21] Appl. No.: 08/596,319

[22] PCT Filed: Apr. 25, 1994

[86] PCT No.: PCT/US94/04540

§ 371 Date: Jan. 31, 1996

§ 102(e) Date: Jan. 31, 1996

[87] PCT Pub. No.: WO94/25565

PCT Pub. Date: Nov. 10, 1994

Related U.S. Application Data

[63] Continuation-in-part of application No. 08/052,560, Apr. 23, 1993, abandoned.

[51] Int. Cl.[6] .............................. C12N 1/20; C12N 9/12; C07H 21/04; C12P 21/06

[52] U.S. Cl. ................... 435/252.3; 536/23.2; 536/23.5; 435/69.1; 435/194; 435/320.1

[58] Field of Search .................................. 435/69.1, 194, 435/320.1, 252.3; 536/23.2, 23.5

[56] References Cited

PUBLICATIONS

Yagi et al. (1994) Bioc. Biophys. Res. Com 200:28–34 "Cloning of the cDNA for the deleted syk kinase homologous to ZAP–70 . . . ".

Chan et al., (1992) Cell 71:649–662 "ZAP–70: A 70 kd protein–tyrosine kinase that associates with the TCR ζ chain".

Taniguchi et al., (1991) J Biol Chem 266: 15790–15796 "Molecular cloning of a porcine gene syk that encodes a 72–KDa protein . . . ".

*Primary Examiner*—Ponnathapura Achutamurthy
*Assistant Examiner*—Tekchand Saidha
*Attorney, Agent, or Firm*—David L. Berstein; Sharon F. Hausdorff; Isabelle M. Clauss

[57] ABSTRACT

The molecular cloning of humansyk DNA, compositions containing same and uses thereof are disclosed.

17 Claims, 4 Drawing Sheets

```
ggctcgag tt(tc) tt(tc) gg(gatc) ca(ag) att ac        syk S1A
ggctcgag tt(tc) tt(tc) gg(gatc) ca(ag) ata ac        syk S1B
ggctcgag tt(tc) tt(tc) gg(gatc) ca(ag) atc ac        syk S1C
 XhoI     F      F      G        Q      I   T cccatcgat cc (ag)tg (ag)aa cca (gatc)gg cat (tc)tt ttc    syk AS2A
cccatcgat cc (ag)tg (ag)aa cca (gatc)gg cat (tc)tt ctc    syk AS2B
 ClaI      G   H     F      W   P       M    K    E ggctcgag tgg atg ct(gat) gt(gatc) atg gaa atg gc          syk S3A
ggctcgag tgg atg ct(gat) gt(gatc) atg gag atg gc          syk S3B
 XhoI     W   M   L       V        M   E   M   A cccatcgat a (ag)tc (atc)ac (ag)tc (ag)ta (ag)ta gtt    syk AS4A
cccatcgat a (ag)tc (atc)ac (ag)tc (ag)ta (ag)ta att    syk AS4B
 ClaI       N      V       V       D       Y   Y   N agt att tg  agc aga acc aga                           syk Probe Z
```

Figure 1A / 2

```
cccatcgat at gat gtt ctt atc ctt gac atg                                    syk ASA
          ClaI   L   I   N   K   D   K   V   H cat gga aac ctg atg aac cag ttc                                             syk ASB
 M   S   V   Q   H   V   L   E gactgctgggtagtccccacctttt                                                   λ for 1
gagcaagttcagcctggttaagtcc                                                   λ for 2
ggggtaaaataacagagagtggcttat                                                 λ rev 1
gagtatttcttccagggtaaaaagc                                                   λ rev 2 cag ccc cgc cga cct ctg cca                                                 syk Probe W
 S   P   A   D   L   C   H cccatcgat cca tca gac tcc tgg gag tgg tag                                   syk ASX
     ClaI  G   D   S   E   Q   S   H   Y ggc ttc ttg agg agg cag acc agg                                             syk ASY
 P   K   K   L   L   C   V   L ggctcgat atg gca gac ag(ct) gc(gc) aa(ct) cac ctg cc                        syk ATG 1
  XhoI    M   A   D   S   A   N   H   L   P ggctcgag atg gca gac ag(ct) gc(gc) aa(ct) cac ttg cc                        syk ATG 2
  XhoI    M   A   D   S   A   N   H   L   P
```

Figure 1B / 2

```
                                                        at gat ggc ctg ctc cag agc ctg a              syk AS QALE
                                                         I   I   A   Q   E   L   A   Q atc acc cgg gag gag gc(at) gaa ga            syk Probe T
                                                         I   T   R   E   E   A   E   D cccatcgat gcc acc cag gta gtt gcg gct ctg    syk ASU
                                                         ClaI     G   G   L   Y   N   R   S   Q ctc ctg gga gtg gta gtg gca gag
                                                     5'-tcaatgaacgatcatgtagcaatgccaattaacccctcgagaattcccaa-3'  syk ASV
                                                         E   Q   S   H   Y   H   C   L
                                                                                        XhoI   EcoRI
                                                                        caattaacccctcgagaattcccaa    Uni 5'-2
                                                        tcaatgaacgatcatgtagcaatgc                    Uni 5'-1
                                                                                         c          Anchor S
                                                                                        c ggagctcttaagggttPO4-5'  Anchor AS
                                                                                  3'-a c
```

Figure 1C / 2

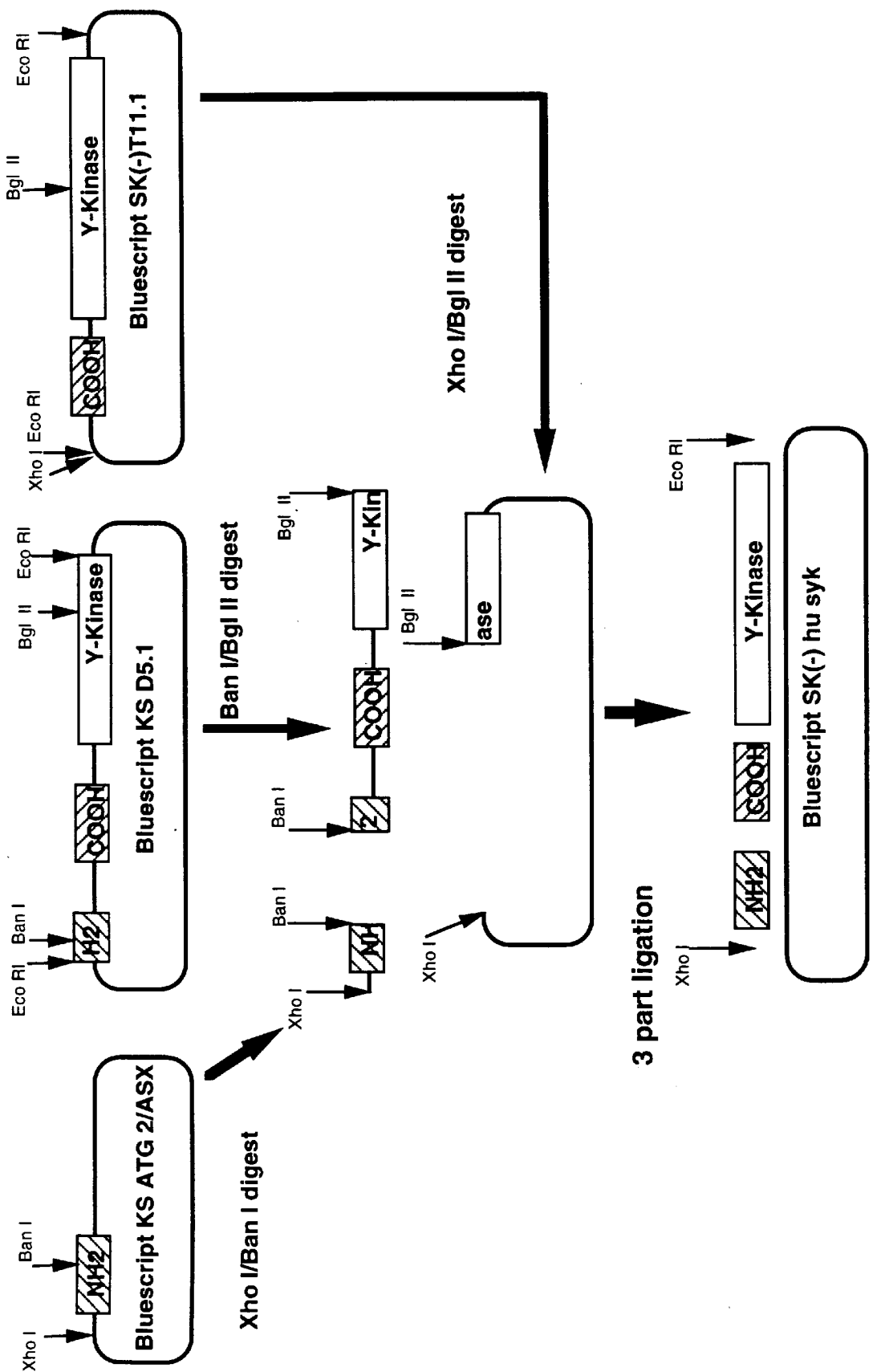
Figure 2/2

HUMAN SYK

RELATED APPLICATIONS

This application is a continuation-in-part of U.S. patent application Ser. No. 08/052,560 filed on Apr. 23, 1993, abandoned.

BACKGROUND OF THE INVENTION

Hypersensitivity is the term applied when an adaptive immune response occurs in an inappropriate or exaggerated form causing tissue damage. Specifically, Type I, or immediate hypersensitivity occurs when the immune response is directed against antigens, such as pollen or house dust mite fecal particles. This Type I response is mediated through immunoglobulin E (IgE) interaction with mast cells and basophils. (IMMUNOLOGY, Roitt, I. M., et al., (eds.) C. V. Mosby Co., St. Louis, Mo., pp. 19.1–19.20 (1989)).

Mast cells and basophils express the high affinity Fc receptor for IgE, designated polyvalent FcεRI. Once IgE binds to the Fcε, subsequent binding of allergen to the IgE molecules caues the receptors to cross-link, triggering the release of cytoplasmic secretory granules containing histamine, and other pharmacological mediators which produce an acute immune reaction (e.g., asthma, dermatitis or rhinitis).

The FcεRI receptor is a complex of three protein subunits, the $\alpha$, $\beta$ and $\gamma$ subunits. The $\beta$ and $\gamma$ subunits have an intracellular domain termed a "tyrosine activation motif" or TAM. TAM motifs and related tyrosine-containing motifs are found on a number of growth factor and primary immune response receptors. Phosphorylation of these motifs by protein tyrosine kinases is thought to play an integral role in receptor activation and cellular signal transduction. (Reth, M., *Nature* 338:383–384 (1989); Koch, C. A., et al., *Science* 252:668–674 (1991); Samuelson, L. E., and Klausner, R. D., *J. Biol. Chem.* 267:24913–24916 (1992)). It has also been shown that a second group of intracellular tyrosine kinases become physically associated with the activated (phosphorylated) receptors and are likely targets of receptor activity (i.e., phosphorylation by the receptor). Phosphorylation of these "second group" proteins initiates additional intracellular signal transduction events which activate biochemical processes within the cell. (Chan, A. C., et al., *Cell* 71:649–662 (1992); Chan, A. C., et al., *Curr. Opin. Immunol.* 4:246–251 (1992); Courtneid, S. A., et al., *Cell Growth Differentiation* 2:483–486 (1991)).

Thus, the protein-protein interaction of activated receptor protein and intracellular kinase protein plays a critical role in intracellular signal pathways. When these pathways are activated inappropriately, such as when the immune system responds to pollens and other allergens, upper respiratory symptoms of allergic rhinitis, wheezing and respiratory distress result. In a severe allergic reaction, life-threatening anaphylaxis can occur.

Currently, treatment of allergies includes avoidance of the allergen, such as the removal of pets from the home or the installation of elaborate air filtration systems to minimize airborne allergens. However, complete removal may be difficult such as when the allergen is ubiquitous as in the case of pollen and dust mites. Pharmacological agents, such as anti-histamines and steroids may also be used in treatment. However, these drugs often produce unwanted side effects, such as drowsiness and gastrointestinal distress. When complete removal of the allergen is impossible, and the allergy cannot be managed with drugs, hyposensitization therapy may be tried. Hyposensitization consists of repeated subcutaneous injections of gradually increasing doses of the responsible allergen. However, hyposensitization therapy is a painful and time-consuming process with unpredictable results. (HARRISON'S PRINCIPLES OF INTERNAL MEDICINE, 12th ed., Wilson, J. D., et al., eds., McGraw-Hill, Inc., New York, N.Y., pp. 1422–1428 (1991)). A significant need exists for materials useful in the design, screening and/or evaluation of effective therapeutic or preventive agents and methods for inhibiting inappropriate or exaggerated response of the immune system to allergens.

SUMMARY OF THE INVENTION

This invention relates to DNA encoding the human form of the protein tyrosine kinase SYK.

In our model, human Syk protein ($p72^{syk}$, hereinafter "Syk") binds to an IgE receptor protein via one or both of the Syk SH2 domains, and thus plays a key role in a signal transduction pathway resulting in mast cell and basophil degranulation and related events. Mast cell and basophil degranulation leads to the release of histamine and other mediators leading to inappropriate or exaggerated immune responses, such as allergic responses, inflammatory responses and asthma.

Our invention encompasses an isolated DNA molecule encoding part or all of the N-terminal portion of human Syk spanning Met-1 up to Gly-180 of SEQ ID NO:2 and allelic variants thereof. ("Isolated" as the term is used herein means removed or separated from materials with which it is normally associated in nature. An isolated DNA molecule thus comprises a cloned DNA sequence separated from other sequences with which is is normally associated, e.g. in a genome or genetic library.) Such isolated DNA molecules of this invention include molecules comprising part or all of the human syk nucleotide sequence spanning A-1 through A-540 of SEQ ID NO:1, or allelic variants thereof.

The isolated DNA molecules of this invention may extend beyond A-540, and include by way of example, DNA molecules comprising the human syk nucleotide sequence of SEQ ID NO:1 and allelic variants thereof.

A DNA molecule containing the nucleotide sequence of SEQ ID NO:1 or an allelic variant thereof may be cloned as described herein, cloned by other methods using the information disclosed herein, synthesized (e.g. by ligation of overlapping synthetic oligonucleotides), excised from our vector pBS (ATCC Accession No.), or combinations of the foregoing.

The DNA sequence depicted in SEQ ID NO:1 was isolated by the mixed oligonucleotide primed amplification of cDNA method (MOPAC). The procedure was carried out in two steps. The first MOPAC step was carried out on a cDNA library obtained from human Daudi cells with degenerate oligonucleotide primers derived from the DNA sequence of the porcine Syk protein described in Taniguchi, T. et al., *J. Biol. Chem.*, 266:15790–15796 (1991). This step resulted in the isolation of a cDNA clone with a cDNA insert containing partial human syk cDNA sequence.

The second MOPAC step was carried out on human basophil cDNA using oligonucleotides derived from both the porcine syk and the human syk partial cDNA sequences. This step also resulted in a partial cDNA sequence. A contiguous human syk cDNA sequence was assembled and cloned resulting in a cDNA insert of 1893 base pairs (SEQ ID NO:1).

In addition to the sequence of SEQ ID NO:1 we have also identified a number of allelic variants containing the following nucleotide substitutions: T-6, C-15, C-18, C-22, C-1050, G-1287 and G-1323. These and other allelic variants of the nucleotide sequence of our SEQ ID NO:1 are encompassed by this invention.

Our invention further includes recombinant DNA constructs consisting of DNA molecules containing the DNA sequence of one of our human syk DNA molecules mentioned above and heterologous DNA. "Heterologous" as the term is used herein means DNA (or amino acid) sequence from a different source or origin relative to the sequence in question. Heterologous sequence may thus originate from a non-human source or from human DNA or human peptide sequence not normally or naturally associated with the sequence in question. The heterologous DNA may be directly linked to a human syk DNA sequence of this invention to encode a fusion protein or peptide (the terms "protein" and "peptide" are used interchangeably herein) containing human Syk peptide sequence linked via peptide bond to heterologous peptide sequence.

Illustrative vectors and associated methodologies useful for making and using fusion proteins which are suitable for use with the human syk DNA molecules of this invention include the well known pGEX vectors for GST fusion proteins (see Smith and Johnson, 1988, Gene 67: 31–41), the pRIT2T Protein A Gene Fusion Vector (Nilsson et al, 1985, EMBO J. 4: 1075), the pEZZ 18 Protein A Gene Fusion Vector (Löwenadler et al, 1987, Gene 58:87; Nilsson et al, 1987, Prot Engineering 1:107; Nilsson et al, 1991, Methods Enzymol 198:3) and He pMC1871 beta-galactosidase Fusion Vector (See e.g., Shapiro et al, 1983, Gene 25:71 and Casabadan et al, 1983, Methods Enzymol 100:293).

Recombinant DNA constructs also include, among others, DNA cloning and expression vectors containing a human syk DNA molecule of this invention and heterologous DNA. The heterologous DNA may include one or more DNA sequences encoding selectable or amplifiable markers, origins of reliplication, transcriptional control elements (promoter and enhancer sequences) and/or other conventional vector elements. Numerous examples of expression vectors for corresponding host cell types (bacterial, yeast, mammalian, insect, etc.) are well known in the art and have been commercially available for several years. Such vectors containing human syk DNA of this invention may be transfected into host cells using known methods. Transfectants may be selected and may be cultured in order to produce the protein encoded by the human syk DNA or construct of this invention.

The human Syk protein so obtained (or truncated or fusion proteins containing part or all of the human Syk peptide sequence) may be structurally characterized and so used in the design of compounds capable of inhibiting its signal transducing function. Such materials may also be used in binding assays to identify compounds capable of binding to Syk and thereby interfering with the normal interactions of Syk with other proteins with which Syk can become associated. Human Syk, a potent tyrosine kinase, may also be used as an enzymatic reagent to catalyze the phosphorylation of tyrosine-containing peptides or proteins. In addition, oligonucleotide primers based on the nucleotide sequence of our SEQ ID NO:1 of may be used in diagnostic PCR procedures to identify cells which are expressing Syk or to identify mutations in Syk, e.g. in biopsy or pathology samples.

The present invention also relates to the recombinantly produced protein encoded by the human syk cDNA sequence. The cDNA insert of the clone described above was sequenced to confirm the open reading frame and the amino acid sequence was deduced. The deduced protein has a sequence of 630 amino acids (SEQ ID NO:2) and a calculated $M_r$ of 72,000. The protein encoded by the human syk cDNA sequence contains two src homology region 2 domains (hereinafter SH2 domains) and one tyrosine kinase domain.

The invention also relates to the use of the recombinantly produced Syk protein, or Syk SH2 domain sequences, or fusion proteins, as research reagents to be used in structure-based drug design to develop TAM mimics or other phosphopeptides or other substances which can interfere with the signal transduction cascade of events leading to allergic responses. The Syk protein, or its SH2 domains, can also be used to develop in vitro binding assays to test the TAM mimics, or other peptides, for activity for subsequent use in the methods described herein.

BRIEF DESCRIPTION OF THE DRAWINGS

FIG. 1A, 1B and 1C shows the oligonucleotide sequences used in the isolation and cloning of the human syk cDNA (see also SEQ ID NOs:3–30).

FIG. 2 is a schematic representation of the three-part ligation used to assemble the full-length human syk cDNA.

DETAILED DESCRIPTION OF THE INVENTION

Human syk DNA was isolated and cloned as described in detail in Example 1. The mixed oligonucleotide primed amplification of cDNA (MOPAC) PCR method of Lee, C. C., et al. (*Science* 1288–1291 (1988)) is the method described herein. However, other standard methods of molecular cloning can also be used.

The MOPAC PCR method of cloning the human syk cDNA was performed in two steps. The first step was carried out on a cDNA library obtained from commercially available human Daudi cells (Burkitt's lymphoma cells). Degenerate oligonucleotide primers for the PCR reactions of the first step were derived from the cDNA sequence of the porcine Syk protein described in Taniguchi, T. et al., *J. Biol. Chem.*, 266:15790–15796 (1991). As described in detail in Example 1, this first step resulted in the isolation of a syk cDNA clone with an insert containing a partial sequence of human syk.

When it became apparent that the Daudi cell library did not contain a full length syk cDNA clone, PCR was performed using a human basophil cDNA as a template in a second series of PCR reactions, also described in detail in Example 1. A contiguous human syk cDNA was assembled via a three-part ligation and transformed into competent bacteria, as described in Example 1 and depicted in FIG. 2. A plasmid, pBS SK(-) hu syk, was subjected to DNA sequencing analysis to confirm that the correct open reading frame of 630 codons for human Syk was present. The nucleotide sequence of the cDNA, 1893 base pairs, is identified in SEQ ID NO:1. The deduced amino acid sequence of human Syk is also shown in SEQ ID NO:2. The sequence has 630 amino acids with an $M_r$ of approximately 72,000.

The deduced human Syk protein sequence exhibits homology with the porcine Syk protein sequence described in Taniguchi, T. et al., *J. Biol. Chem.*. 266:15790–15796 (1991). Neither deduced amino acid sequence contains a ligand binding or membrane-spanning region, suggesting that the Syk protein is not associated with the cell membrane (i.e., a non-receptor protein). However, both human and porcine Syk contain two src homology region 2 domains (SH2 domains), one at the N-terminal ($SH2_N$) and one at the C-terminal ($SH2_C$) and one protein tyrosine kinase domain.

Src homology region 2 (SH2) domains are noncatalytic domains that are conserved among a series of cytoplasmic signaling proteins regulated by receptor protein tyrosine kinases (Koch, C. A., et al. *Science* 252:668–674 (1991). The SH2 domain contains approximately 100 amino acids and was first shown to be a nonkinase domain conserved between the src and fps gene products. (Songyang, Z., et al., *Cell* 72:767–778 (1993). Now, more than 20 cytosolic proteins likely to be involved in signaling events have been shown to contain SH2 domains. (Songyang, Z., et al., *Cell* 72:767–778 (1993). The SH2 domains of these signaling proteins bind tyrosine phosphorylated polypeptides in a sequence specific manner.

Tyrosine phosphorylation of a receptor, (i.e., activation of a receptor) acts as a switch to induce the binding of these signaling protein kinases via their SH2 domains, thereby mediating the formation of heteromeric protein complexes at, or near, the plasma membrane. The formation of these complexes is thought to control the activation of intracellular signal transduction pathways. (Koch, C. A., et al. *Science* 252:668–674 (1991).

A number of primary immune response receptors on T cells and B cells, and the IgE receptor on mast cells and basophils share a common amino acid motif present in their cytoplasmic tail. (Samuelson, L. E. and Klausner, R. D., *J. Biol. Chem.* 267:24913–24916 (1992); Reth, M., *Nature* 338:383–384 (1989)). This common motif, 18–27 amino acids long, has been termed the "tyrosine activation motif" or TAM.

The function of the TAM motif has been studied for the T cell receptor (TCR). (Romeo, C. et al., *Cell* 68:889–897 (1992)). Activation of the TCR by antigen results in crosslinking of TCR ζ subunits, leading to phosphorylation of a TAM in the TCR by a protein kinase. The phosphorylation of TAM motifs is believed to be critical for TCR activation because of evidence that the substitution of a phenylalanine residue for either tyrosine residue in the TAM motif of the ζ subunit of the TCR blocked T cell activation of IL-2 production. (Letoumer, F. and Klausner, R. D., *Science* 255:79–82 (1992)).

After phosphorylation, the activated TCR has been shown to be associated with a 70 kD protein tyrosine kinase, termed ZAP-70, which also undergoes subsequent phosphorylation. (Chan, A. C., et al., *Cell* 71:649–662 (1992). It is believed that assembly of the ZAP-70 protein-TCR complex, via the ZAP-70 SH2 domains interaction with phosphorylated TCR TAM motifs, results in additional levels of regulation of TCR signaling. (Chan, A. C., et al., *Cell* 71:649–662 (1992).

It has also been shown that activation of rat basophil leukemia cells (RBL cells) by antigen cross-linking of IgE molecules bound to the IgE receptor (FcεRI) results in rapid and sustained activation of tyrosine phosphorylation of multiple RBL proteins. (Benhamou, M. V., et al., *J. Biol. Chem.* 267:7310–7314 (1992); Li, W., et al., *Mol. Cell Biol.* 12:3176–3182 (1992)). Two protein tyrosine kinases have been implicated in these phosphorylation events. The first kinase, lyn, is a protein tyrosine kinase belonging to the family of src protein kinases. (Wiseman, E., and Bolen, J. B., *Nature* 355:78–80 (1992); Seidel-Dugan, C., et al., *Mol. Cell Biol.* 12:1835–1845 (1992)). Lyn is activated (phosphorylated) transiently (1–5 min) following antigen incubation and appears to co-precipitate with the IgE receptor in immunoprecipitation experiments.

A second protein tyrosine kinase, Syk, has been shown to be activated after IgE receptor crosslinking with antigen and is associated in a complex with the IgE receptor (Hutchcroft, J. E., et al., *Proc. Natl. Acad. Sci. USA* 89:9107–9111 (1992)). In our model, Syk binding to the IgE receptor is mediated by binding to phosphorylated TAM motifs in the β or γ subunit of the IgE receptor. Assembly of this human Syk protein-IgE receptor complex results in regulation of IgE receptor signaling, such as mast cell degranulation.

In our model, lyn phosphorylates the tyrosine residues of the TAM motifs of the β and γ subunits of the IgE receptor. Syk then binds to the phosphorylated TAM motifs through its SH2 domains. Activation (i.e., phosphorylation) of Syk can be mediated by this binding, by lyn phosphorylation, or another mechanism. In any event, the assembly of a Syk protein-IgE receptor complex, via the syk SH2 domains interaction with the IgE receptor TAM, results in additional levels of regulation of IgE receptor signaling.

Inhibition of the interaction of Syk and the IgE receptor, e.g. via the Syk SH2 domains and the receptor phosphorylated TAM motif, interrupts the cascade of signaling events leading to mast cell or basophil degranulation, allergic responses, inflammatory responses or any other inappropriate or exaggerated immune response.

For example, molecules that specifically interfere with the interaction of the syk SH2 domain and the TAM motif would mimic the structure of the TAM binding site (peptide mimics), and bind to the SH2 domain of Syk, thereby preventing Syk from binding to TAM on the receptor and, thus, preventing, reducing, or completely eliminating the response of the receptor to the stimuli.

TAM motifs from different receptor subunits appear to specifically activate distinct biological responses in different cell types. Therefore, TAM mimics are designed to mimic the TAM motifs of specific receptors. For example, the TAM motif of the ζ subunit on the T cell receptor is different from the TAM motif on the β and γ subunits on the IgE receptor of mast cells. Thus, a TAM mimic for the TCR TAM would not be as effective in inhibiting the binding of Syk to the IgE receptor.

In one embodiment, the activation of mast cells and basophils leading to degranulation, is inhibited with a peptide which mimics a phosphorylated TAM of the β or γ subunit of the IgE receptor. Such TAM mimics can be synthesized according to the methods disclosed in U.S. Ser. No. 08/013,414, the teachings of which are incorporated herein by reference.

The TAM mimics can inhibit the activation of mast cells and basophils by blocking the association of the Syk protein with the activated IgE receptor. They mimic the phosphorylated TAM on the IgE receptor and bind directly to the SH2 domain of the Syk protein. Thus, the TAM mimics act as competitive antagonists.

The TAM mimics used in the methods described herein can be peptides (comprised of natural and non-natural amino acids) or can be peptide analogs (comprised of peptide and non-peptide portions). All TAM mimics used in these methods have specific characteristics pertaining to biological activity. These characteristics include the ability of the phosphotyrosine residues, to bind to the SH2 domain of Syk, and retention of a biologically active conformation.

The TAM mimics used in the methods described herein include at least five amino acid residues and generally have a sequence in the range of 15–39 amino acid residues. However, longer mimics can be used (e.g., up to the total length of an SH2 domain which is characteristically approximately 100 amino acid residues) if they have the desired characteristics described above. Shorter mimic sequences would have the distinct advantage that they exhibit lesser charge than longer sequences which would facilitate membrane penetration and cell entry. Shorter mimics would also be less susceptible to enzymatic degradation and less subject to the conformational constraints required for biological activity.

Although the methods described herein preferably use TAM mimics, peptide and peptide analog mimics of the SH2 domains of the Syk protein can also be used in the methods described herein. The SH2 mimic would also block the association of the Syk protein with the activated IgE receptor as a competitive antagonist, thus, inhibiting mast cell degranulation or other inappropriate or exaggerated immune responses.

TAM mimics and SH2 mimics can be screened for biological activity (i.e., the ability to block the association of syk with the activated receptor) using art-recognized in vitro assays. For example, peptide capture assays can be used in which recombinant SH2 domains (for TAM mimic screening) or TAM sequences (for SH2 screening) are immobilized in plastic microtiter wells. Labeled non-phosphorylated or phosphorylated peptides are then added to these wells, and incubated under conditions sufficient for binding to take place. Unbound labeled peptide is then removed and the amount of bound peptide is determined. The TAM or SH2 mimics exhibiting the highest per cent binding to bound peptide have the greatest potential for use in the methods described herein.

Biospecific Interaction Analysis (BIA) in real time can also be performed to evaluate biological activity. Surface plasmon resonance (SPR), which is the basis for BIA measurements, is an optical phenomenon arising in metal films under conditions of total internal reflection. The phenomenon produces a sharp dip in the intensity of reflected light at a specific angle. The position of this resonance angle depends on several factors, including the refractive index of the medium close to the non-illuminated side of the metal film. Refractive index is directly related to the concentration of dissolved material in the medium. By keeping other factors constant, SPR is used to measure changes in the concentration of macromolecules in a surface layer of solution in contact with a dextran-coated gold film. As described in detail in Example 2, using the BIAcore™ instrument from Pharmacia Biosensor AB, the association and dissociation rate constants for a peptide binding to the SH2 domain of a protein kinase, PI3K, have been measured. The association and dissociation rate constants for peptide mimics binding to SH2 domains of Syk can also be measured under similar conditions. Peptide mimics exhibiting higher association constants ($K_a$) have the greatest potential for use in the methods described herein.

In particular, mast cell or basophil degranulation assays can be used to measure in vitro activity of TAM or SH2 mimics. The release of histamine, the release of beta-hexosaminidase, the release of cytokines and/or increased phosphatidylinositol hydrolysis or tyrosine phosphorylation can be detected in in vitro assays as an indication of biological activity. (Stephan, V. M., et al., *J. Biol. Chem.* 267:5434–5441 (1992)). For example, histamine release can be measured by radioimmunoassay using a kit available from AMAC Inc. (Westbrook, Me.).

A known mast cell/basophil degranulation assay is described in detail in Example 3. Briefly, mast cells and basophils express the FcεRI receptor on their cell surface. This receptor binds the Fc portion of IgE antibody with high affinity. Binding of multivalent antigens activates the process that leads to degranulation (the release of preformed secretory granules) and the stimulation of the production of a number of cytokines. The assay has two variations: an intact cell assay and a permeabilized cell assay. For testing peptides and small molecules where membrane permeability is questionable, the cells are permeabilized using streptolysin O. Tyrosine kinase inhibitors, such as leflunomide and its active metabolite, A771726, vanadate and genistein, are used as controls to establish whether known inhibitors of mast cell degranulation show inhibitory activity. Thus, if a TAM mimic interferes with degranulation, it has the greatest potential for use in the methods described herein.

TAM mimics can also be evaluated for biological activity using immunoprecipitation assays or receptor association assays such as described in Matsuda, M., et al., *J. Biol. Chem.* 268:4441–4446 (1993) and Escobedo, J. A., et al., *Mol. Cell. Biol.* 11:1125–1132 (1991). The basic protocol is to lyse the cells of interest in a gentle buffer with detergent that would preserve natural in vivo protein-protein interactions, creating a detergent solubilized cytoplasmic lysate, and a particulate/detergent insoluble fraction. The detergent soluble lysate is then added to a quantity of human Syk SH2 domain fusion protein and mixed gently for a period of time sufficient to allow relatively high affinity interactions to form between the introduced fusion protein and any cellular proteins. The fusion proteins are purified by centrifugation from the lysate, and washed several times with lysate buffer to remove any non-specific or low affinity interactions. The proteins that remain associated with the fusion protein are then dissociated from the fusion protein, and analyzed by denaturing gel electrophoresis. The eluted proteins are then visualized by any number of methods. For example, a western blot of the SDS gel, probed with anti-phosphotyrosine antibody, can be used to visualize phosphotyrosine containing proteins.

The cells can also be metabolically labeled (that is, "fed" label in culture) so as to label either all proteins (with $^{35}S$ labeled methionine and cysteine) or to label phosphoproteins (with $^{32}P$ orthophosphate). After the denaturing gel electrophoresis, the proteins are visualized by autoradiography.

Antibodies specific for various components of the mast cell IgE receptor complex can be used to directly determine, either by immunoprecipitation or western blot, whether those specific components are interacting with the SH2 fusion proteins in extracts of either resting or activated RBL cells by addition of IgE and hapten. Differences in the proteins associated with the SH2 fusion proteins should be observed between resting and activated cells, reflecting the changing interactions of human Syk upon mast cell activation. By identifying those proteins that associate, or disassociate, upon activation, one may identify cellular proteins that directly interact with human Syk during mast cell activation.

Moreover, antibodies, either polyclonal or monoclonal, can be produced that are immunoreactive with one or both of the SH2 domains of the Syk protein. Such antibodies can be made by standard laboratory techniques. By screening the SH2 antibodies, one may obtain specific antibodies which also block the association of the Syk protein with the activated IgE receptor thus, inhibiting mast cell degranulation or other inappropriate or exaggerated immune responses.

Anti-Syk SH2 domain antibodies can be evaluated for biological activity using standard laboratory techniques such as radioimmunoassay or ELISA. Immunoprecipitation assays, or receptor association assays, such as those described above, can also be used.

TAM mimics, SH2 mimics, and antibodies demonstrating the desired activity in vitro can be tested in vivo for inhibitory activity. For example, TAM mimics can be tested in suitable animal model systems including rats, mice, or horses. There are numerous animal models of asthma that have been developed and can be used (for reviews, see Larson, "Experimental Models of Reversible Airway Obstruction", in THE LUNG, Scientific Foundations, Crystal, West et al. (eds.), Raven Press, New York, pp. 953–965 (1991); Warner et al., 1990, Am. Rev. Respir. Dis. 141:253–257). Species used as animal models for asthma include mice, rats, guinea pigs, rabbits, ponies, dogs, sheep and primates. Other in vivo models available are described in Cross et al., Lab Invest. 63:162–170 (1990)); and Koh, et al., Science 256:1210–1213 (1992)).

TAM mimics, SH2 mimics and antibodies which inhibit degranulation of mast cells and basophils are preferred for treatment or prevention of type I allergic (IgE-mediated) reactions such as asthma and allergic rhinitis, diseases and disorders associated with an inappropriate or exaggerated immune system response, or inflammation. The preferred method of treatment, or prevention, is by administrating to a mammal an effective amount of a peptide, or peptide analog which mimics a phosphorylated TAM which blocks the association of the Syk SH2 domain with the activated IgE receptor.

Diseases and disorders which can be treated by administration of an effective amount of a TAM mimic, SH2 mimic, or antibody which inhibits inappropriate or exaggerated inflammatory/immune responses include inflammatory arthritis (e.g., rheumatoid arthritis, seronegative spondyloarthritites (Behcets disease, Reiter's syndrome, etc.), juvenile rheumatoid arthritis, vasculitis, psoriatic arthritis, polydermatomyositis); systemic lupus erythematosus (SLE); asthma; inflammatory dermatoses (e.g., psoriasis, dermatitis herpetiformis, eczema, necrotizing and cutaneous vasculitis, bullous diseases); inflammatory bowel disease (e.g., Crohn's disease and ulcerative colitis); tissue damage relating to tissue transplantation; and other autoimmune disorders.

Additional disorders such as glomerulonephritis, juvenile onset diabetes, multiple sclerosis, allergic conditions, autoimmune thyroiditis, allograft rejection (e.g., rejection of transplanted organs such as kidney, heart, pancreas, bowel or liver), and graft-versus-host disease can also be treated.

Furthermore, in a preferred aspect of the invention, a TAM mimic which inhibits mast cell and basophil degranulation is administered to treat, or prevent, a type I allergic reaction such as one or more of the following: atopic diseases (e.g., allergic rhinitis, commonly known as hayfever, due to pollens, fungal spores, dust, animal dander, asthma, atopic dermatitis, and allergic gastroenteropathy due to ingested food); anaphylaxis (a systemic immediate hypersensitivity affecting multiple organs, due to, for example, drugs, proteins such as in vaccines, and nonproteins such as antibiotics, anesthetics, salicylates, foods, venom of stinging insects); and urticaria or a angioedema (increased cutaneous vascular permeability). Mammals include horses, cattle, dogs, cats and humans.

Various delivery systems are known and can be used to administer a TAM mimic. For example, encapsulation in liposomes, microparticles, microcapsules, expression by recombinant cells, receptor-mediated endocytosis, construction of a TAM mimic-encoding nucleic acid as part of a retroviral or other vector can be used. Methods of introduction for both peptide mimics and antibodies include, for example, intradermal, intramuscular, intraperitoneal, intravenous, subcutaneous, intranasal, epidural, and oral routes. Any other convenient route of administration can be used, for example, by infusion or bolus injection, by absorption through epithelial or mucocutaneous linings (e.g., oral mucosa, rectal and intestinal mucosa, etc.) and the TAM mimic may be administered together with other biologically active agents. Administration can be systemic or local.

For TAM mimics which are used for inhibition of mast cell activation, e.g., for therapy of asthma or allergy, the preferred route of administration is nasal or via a bronchial aerosol. In particular, a bronchial aerosol is employed. Pulmonary administration can be accomplished, for example, using any of various delivery devices known in the art (Newman, S. P., AEROSOLS AND THE LUNG, Clarke and Davia (eds., Butterworths, London, England, pp. 197–224 (1984); PCT Publication No. WO 92/16192, PCT Publication No. WO 91/08760. Delivery devices include, for example, nebulizers, metered dose inhalers, and powder inhalers. Various delivery devices are commercially available and can be employed, e.g., Ultravent nebulizer (Mallinckrodt, Inc., St. Louis, Mo.); Acorn II nebulizer (Marquest Medical Products, Englewood, Colo.), Ventolin metered dose inhaler (Glaxo Inc., Research Triangle park, N.C.); Spinhaler powder inhaler (Fisons Corp., Bedford, Mass.). Such devices typically entail the use of formulations suitable for dispensing from such a device, in which a propellant material may be present.

A nebulizer may be used to produce aerosol particles, or any of various physiologically acceptable inert gases may be used as an aerosolizing agent. Other components such as physiologically acceptable surfacatants (e.g., glycerides), excipients (e.g., lactose), carriers, and diluents may also be included.

In another embodiment, it may be desirable to administer the peptide mimics or antibodies of the invention locally to the area in need of treatment. This may be achieved by, for example, local infusion during surgery, topical application (e.g., for skin conditions such as psoriasis), by injection, by means of a catheter, by means of a suppository, or by means of an implant, said implant being of a porous, non-porous, or gelatinous material, including membranes, such as sialastic membranes, or fibers.

The invention also relates to the purified recombinantly produced intact Syk protein and purified recombinantly produced SH2 domains. Expression vectors can be constructed using routine laboratory methods to express the intact human Syk protein, or any of its various peptide domains, especially the SH2 domains. Proteins and peptides can be expressed as a component of a fusion protein, such as a protein in which the other component is a "tag" such as with a glutathione-Stransferase (GST) enzyme tag or a polyhistidine tag, to facilitate purification. Alternatively, the proteins can be expressed alone, (i.e., not as a member of a fusion protein). Proteins expressed as fusion proteins or alone, can be purified by standard laboratory methods, such as column chromatography or electrophoretic techniques.

A fusion protein in which the C-terminal S2 domain of human Syk is linked to GST has been produced as described in Example 4. In this embodiment, the C-terminal SH2 domain was cloned into the pGex fusion vector system. This vector provides a fusion site with GST at the N-terminus, followed by a protease cleavage site directly preceding the protein to be fused. The fusion proteins are generated in *E. coli,* and purified by absorption to agarose beads containing glutathione.

The SH2 domain constructs can be assayed for their activity using the in vitro transcription/translation assay as described in Example 5. The purpose of this assay is to determine if the SH2 domains are functional via binding to phosphotyrosine and to develop additional assays to screen and identify peptides and peptide mimics which bind to these SH2 domains.

The purified recombinant Syk protein and Syk SH2 domains can be used to determine the affinity of the two Syk SH2 domains for binding to the TAM motifs from the β and γ subunits of the IgE receptor and to determine the minimal region of the TAM motif that can bind to the Syk SH2 domain. This information can be used for the design of inhibitors that block IgE receptor activation.

The recombinant Syk protein and Syk SH2 domains can also be used to determine the structure of the phosphorylated TAM motif when bound to the Syk SH2 domains. For example, in order to design small molecules that mimic the structure of the phosphorylated TAM motif, it is helpful to know the structure of the TAM peptide sequence when bound to the Syk SH2 domain. Since short peptide sequences like the TAM motif have flexible structures in solution, it is useful to examine their structure when bound to their binding partner in order to design molecules that mimic their structure. The structure of the phosphorylated TAM motif bound to Syk SH2 domains can be derived using X-ray crystallography and NMR spectroscopy. This structural information can be used to design additional TAM mimics. Once these mimics are synthesized, their structure can be examined when bound to Syk SH2 domains in order to further optimize the design of molecules that "best fit" in Syk.

The recombinant Syk protein and Syk SH2 domains can further be used to derive assays that determine the binding affinity of the TAM mimetic compounds for Syk SH2 domains. These assays can be used to determine whether candidate inhibitory molecules interfere with the binding of Syk SH2 domains to phosphoTAM motifs from the β and γ TAM motifs.

Moreover, variant recombinant sequences of the Syk protein and SH2 domains can be constructed for use in dominant negative expression studies in which mutant forms of the Syk protein, or Syk SH2 domains, are expressed that dominantly interfere with the binding of wild type Syk protein with the activated IgE receptor. Studies such as these can lead to further elucidation of the signal transduction cascade of events.

The present invention will now be illustrated by the following examples which further and more specifically illustrate the invention.

EXAMPLE 1

Isolation and Cloning of a Human syk

A λ gt10 cDNA library derived from Human Daudi cells' (Burkitt's Lymphoma, ATCC# CCL 213) mRNA was purchased from a commercial source (Clontech Laboratories Inc., Catalog #HL 1117a, random + oligo dT primed). Phage from the bacterial lysate were used as a template to amplify the library in the MOPAC PCR reaction described by Lee, C.C. et al., *Science* 239:1288–1291 (1988). Primers for the aforementioned PCR reactions were derived from the DNA sequence of the porcine pp72 syk protein described by Taniguchi, T. et al.,*J. Biol. Chem.* 266:15790–15796 (1991).

Two pairs of degenerate primers were synthesized based on relatively non-degenerate regions of the porcine syk cDNA: 1) the 5' end of the NH2 terminal SH2 domain (sense primer) and the 5' end of the COOH terminal SH2 domain (antisense primer) and 2) a portion of the kinase domain spanning about 200 amino acids. These primers labeled S1, AS2 and S3, AS4 respectively, (SEQ ID NOS: 3–11), are depicted in FIG. 1A and 1B. To reduce the degeneracy of these oligo primer pairs, multiple versions of each oligo were synthesized and used in multiple combinations in MOPAC PCR so that at least the last five 3' bases would exactly match the syk cDNA in at least one reaction. Hence the oligonucleotide primers listed in FIG. 1A and 1B are S1A, S1B, S1C, (SEQ ID NOS: 3, 4, 5) and AS2A, AS2B (SEQ ID NOS: 6, 7), etc.

All reactions were performed in duplicate in an MJ Research Minicyler using the following cycling program at two different annealing temperatures (55° C. or 60° C.) under these ionic conditions:

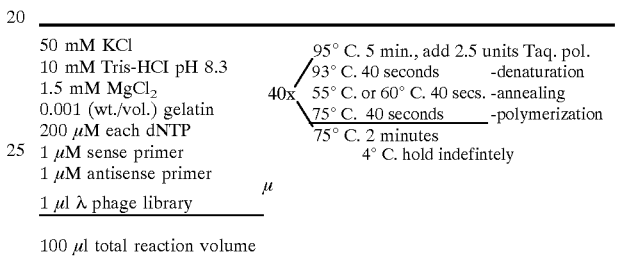

50 mM KCl
10 mM Tris-HCI pH 8.3
1.5 mM MgCl₂
0.001 (wt./vol.) gelatin
200 μM each dNTP
1 μM sense primer
1 μM antisense primer
1 μl λ phage library 100 μl total reaction volume 10 μl aliquots of each reaction were analyzed by agarose gel electrophoresis for amplification of DNA fragments of the predicted size. No amplifications products were observed in reactions using the any of the S1 (SEQ ID NOS: 3–5) and AS2 (SEQ ID NOS: 6 and 7) primer pairs based on the SH2 region of Syk. However, DNA fragments approximately 600 base pairs in length, sufficient to encode approximately 200 amino adds of the kinase domain of Syk, resulted from amplifications employing the S3B (SEQ ID NOS: 8 and 9) and AS4A (SEQ ID NOS: 10 and 11) primer pairs.

The remaining 90 μl of the S3B/AS4A reaction were phenol-chloroform extracted, ethanol precipitated and digested with the restriction endonucleases Xho I and Cla I which had been included at the 5' ends of the sense and antisense oligonucleotide primers, respectively. Simultaneously, the vector Bluescript KS+ was digested with Xho I and Cla I. DNA fragments from both reactions were resolved on a 0.5% (wt./vol.) low-melt agarose (NuSieve GTG or SeaPlaque GTG, FMC Corp.) gel, excised, melted at 70° C., and ligated for one hour at room temperature with T4 DNA ligase (Pharmacia). The ligations were melted at 70° C. and transformed into competent DH5a bacteria (Gibco-BRL) according to the manufacturer's instructions, the bacteria spread onto BHI (Difco) agar plates supplemented with 200 μg/ml ampicillin (Sigma Corp.), and the plates incubated overnight at 37° C. Six colonies were inoculated into 4 ml BHI cultures supplemented with 200 μg/ml ampicillin, and the 4 ml cultures were shaken overnight at 37° C. Plasmid DNA was prepared using a miniprep kit (Qiagen Corp.), subjected to digestion with Xho I and Cla I, and analyzed by agarose gel electrophoresis. Plasmid from three of the colonies were positive for an Xho I/Cla I fragment roughly 620 bp in length, and were subsequently subjected to double stranded DNA dideoxy sequence analysis (Sequenase 2.0, U.S. Biochemicals). The DNA sequence of the 5' ends of the inserts within the three plasmids was identical. Translation of the DNA sequence revealed extensive homology with the porcine Syk protein sequence. Within the first 47 amino adds of the human syk partial cDNA clones, the only difference detected with porcine syk was position 481 with a substitution of serine for cysteine.

In an attempt to done the 5' end of the human syk cDNA, nested antisense nondegenerate oligonucleotide primers derived from the 5' end of the aforementioned human syk partial cDNA clone were synthesized (ASA (SEQ ID NO: 13) and ASB (SEQ ID NO: 14), FIG. 1A and 1B). These were to be used in conjunction with λ left or λ right arm primers (from the region bounding the Eco RI cloning site in λ gt10) to amplify the 5' end of the insert in phage harboring human syk cDNA from the Daudi λ gt10 library. To verify the authenticity of PCR products as syk cDNAs, another oligonucleotide, probe Z (SEQ ID NO: 12), was synthesized for use in Southern and colony hybridization analysis.

Primary PCR reactions were carried out using either the λ for 1°/ASB (SEQ ID NOS: 15 and 14 respectively) or λ rev 1°/ASB (SEQ ID NOS: 17 and 14 respectively) primer pair with the program described above, with the exception that the annealing temperature was either 60° C. or 65° C. and polymerization was allowed to proceed for 2 minutes 30 seconds. A secondary reaction ensued, using 1 µl of the primary reaction as template, with either the λ for 2°/ASA (SEQ ID NOS: 16 and 13 respectively) or λ rev 2°/ASA (SEQ ID NOS: 18 and 13 respectively) primer pair, and the same annealing temperature used in the primary amplification. Agarose gel electrophoretic analysis of the secondary PCR products revealed a smear from approximately 2 kb to the bottom of the gel, with discrete bands scattered throughout the smear in the λ rev 2°/ASB reaction. An alkali transfer of the gel was made onto charged nylon membrane (Qiabrane Plus, Qiagen Inc.) using a BioRad 785 Vacuum Blotter according to the manufacturer's protocol. After neutralization the blot was placed in oligohybmix (6×SSC, 5×Denhardt's solution, 1% SDS, 10 mM NaPO$_4$, 200 µg/ml denatured salmon sperm DNA) and allowed to prehybridize for one hour at 50° C. Z probe was labeled with $^{33}$P-γ-ATP using T4 polynucleotide kinase (Pharmacia) under standard conditions (Sambrook, et al., Molecular Cloning: A Laboratory Manual (Cold Spring Harbor Lab., Cold Spring Harbor, N.Y.) (1989)). The probe was purified from unincorporated $^{33}$P using a spin column made with Sephadex G-25 (Pharmacia), and added to the blot. Hybridization at 50° C. proceeded overnight, after which the blot was washed 3×20 minutes at 55° C. in 2×SSC/1% SDS and subjected to autoradiography. Probe hybridized to the blot in a pattern that mirrored the smear with discrete bands visualized by ethidium bromide staining of the gel, indicating that the amplified DNA products were derived from human syk cDNA.

The remainder of the λ rev 2°/ASA (65° C.) secondary reaction was phenolchloroform extracted, ethanol precipitated and digested with the restriction endonucleases Xho I and Cla I and resolved on a 0.5% (wt./vol) low-melt agarose gel. A band of approximately 1.2 kb was excised, melted at 70° C., and ligated into Xho I/Cla I digested Bluescript KS+ plasmid. Plasmid prepared from colonies arising from transformation of the ligation was analyzed by agarose gel electrophoresis after digestion with Xho I and Cla I restriction endonucleases. Several of the plasmids contained 1.2 kb inserts whose 5' ends were analyzed by DNA sequence analysis. The amino acid sequence deduced from these partial cDNAs is quite homologous with that of porcine Syk, and extend NH$_2$ terminal to the serine 79 residue of the protein. Hence the amplified partial cDNA was roughly 240 bp too short to encode the 5' end of the human syk cDNA.

Further attempts made to isolate a partial cDNA with the 5' end of the human syk gene were performed in an analogous manner. Nested antisense nondegenerate oligonucleotide primers derived from the 5' end of the above partial cDNA clone were synthesized (ASX and ASY (SEQ ID NOS: 20 and 21), FIG. 1A and 1B) in conjunction with λ left or λ right arm primers. DNA fragments generated using these primer pairs hybridized to Probe W (SEQ ID NO: 19) on Southern blots, proving the fragments were specific for the 5' end of human Syk. However, none of the amplified fragments were greater than 180 bp in length, and were therefore insufficient to encode the initiator codon of human Syk.

Concomitantly, 800,000 plaques of the λ gt10 Daudi cell cDNA library were screened with $^{32}$P nick-translated (Stratagene Prime-It) 0.6 kb fragment from the human syk kinase domain (S3B/AS4A). Hybridization and washing of duplicate filters (Hybond N+, Amersham) according to Church and Gilbert protocol buffers, at 65° C. led to 55 initial positives, 27 of which were positive on secondary plating and hybridization as above.

Eleven of the secondaries were screened for insert size by PCR amplification, using the syk kinase domain oligo ASB with the λ for 1° or λ rev 1° primers. Four clones yielding the largest PCR products were chosen for further characterization by subcloning and sequencing. (D1.2, 3.2, 8.2, 10.2) From these λ clones, partial sequence of human syk cDNA, from the COOH-terminal SH2 domain to the 3' untranslated region, was determined.

When it became apparent that the Daudi cell λ gt10 library probably did not contain a full length syk cDNA clone, PCR was performed using human basophil cDNA as template in order to obtain the gene's 5' end. Basophils were purified from 60 ml of freshly drawn blood using Percoll step gradient according to the protocol of Warner, J. A., et al. *J Immunol. Methods* 105:107–110 (1987). Basophils removed from the gradient's interface were washed 2× in PBS+4 mM EDTA, and the cell pellet lysed in guanidine thiocyanate buffer (Chirgwin, J. M., et al., *Biochem.*, 18:5294–5299 (1979)). RNA was purified by acid phenol extraction. One tenth of the total RNA was reverse transcribed with Superscript reverse transcriptase (Gibco-BRL) according to the manufacturer's instructions.

A pair of "guessmer" oligonucleotides based on the first nine amino acids of porcine Syk with biased codon selection (Syk ATG1 and Syk ATG2, (SEQ ID NOS: 22 and 23), FIG. 1A and 1B) were synthesized for use as a primers in conjunction with the antisense primers ASX and ASY (SEQ ID NOS: 20 and 21) in PCR amplification of the 5' end of human syk. The design of these guessmers was aided by the consideration of nucleotide sequence of the first nine amino acids of the Syk related protein in T cells, ZAP-70 (Chan, A. C., et al., *Cell*, 71:649–662 (1992)).

A DNA fragment encoding the 5' end of the coding sequence of syk was amplified in a series of nested PCR reactions using either Syk ATG 1 or Syk ATG 2 as the sense primer in both reactions, and ASY and ASX in the primary and secondary reactions respectively. A standard cycling protocol was employed, with annealing of the primers at either 60° C. or 65° C. A DNA fragment of the expected size (~280 bp) arose from the amplification, and after subcloning (Bluescript KS ATG 2/ASX), DNA sequence analysis confirmed its authenticity as a partial 5' syk cDNA.

Because of the high error rate of Taq DNA polymerase, (Keohavong, P. and Thilly, W. G., *Proc. Natl. Acad. Sci.*, USA 86:9253–9257 (1980)). DNA sequence from the single 5' partial cDNA was not 100% reliable, and direct cycle sequencing of a population of PCR amplified cDNA fragments was carried out. Direct sequencing of a population of PCR products effectively "neutralizes" the effect of Taq DNA polymerase infidelity (Gyllensten, U. B., and Ehrlich, H. A., *Proc. Natl. Acad. Sci. USA,* 85:7652–7656 (1988)). A DNA fragment encoding the first 140 amino acids of human Syk was amplified from human basophil cDNA (using the Syk ATG2/AS QALE primer pair (SEQ ID NOS: 23 and 24) isolated on a low melt agarose gel and employed as template in cycle sequencing reactions using a kit (Gibco-BRL). Both primers were $^{33}$P end labeled and used to obtain complementary sense and antisense DNA sequence data. This sequence data, in conjunction with that obtained from the λ phage clones, definitively determined the coding sequence for all but the first nine amino acids of the human Syk protein. Anchored PCR was then used to identify these remaining nine codons and any additional 5' untranslated sequence.

Double stranded cDNA was synthesized from total human basophil RNA using a kit (Gibco-BRL) based on the method of Gubler, U., and Hoffman, B. J., *Gene* 25:263–269 (1983). After the double stranded cDNA was blunted with T4 DNA polymerase (Pharmacia), an "anchor" (SEQ ID NO: 30, Anchor S and branched Anchor AS, FIG. 1A and 1B) was ligated onto its ends using T4 DNA ligase (Pharmacia). The anchor was a variant of that described by Roux, K. H. and Dhanarajan, P., *Biotechniques:* 8:48–57 (1990), in that it was designed to ligate to blunted ended rather than restriction digested DNA fragments. However, like the anchor of Roux and Dhanarajan, only the 5' end which is a substrate for ligation is phosphorylated, and the other 5' end cannot hybridize to the partner strand of the anchor due to the introduction of a four base pair mismatch. This mismatch minimizes non-specific priming during PCR amplification by preventing the DNA strand covalently linked to the anchor from participating in amplification unless its complementary strand has first been specifically primed by the antisense oligonucleotide in the reaction. The syk-specific antisense primers used in the amplification of the 5' end of the syk gene, ASU and ASV (SEQ ID NOS: 26 and 27, FIG. 1A and 1B), were derived from the N terminal SH2 domain sequence determined by the above cycle sequencing. For detection of 5' Syk specific amplification products, Probe T (SEQ ID NO: 25), encoding sequence just 5' of ASU, was also synthesized. Two consecutive PCR amplifications with nested primer pairs (1°: Uni 5'-1/ASV (SEQ ID NOS: 29 and 27 respectively), and 2° Uni 5'-2/ASU (SEQ ID NOS: 28 and 26 respectively) and the "anchored" double stranded human basophil cDNA template were carried out under standard conditions, with an annealing temperature of 65° C. Very small DNA products (on the order of 100 bp) generated by these reactions were subcloned into Bluescript KS+ as Xho I/Cla I fragments, and sequenced. The sequence of two different inserts confirmed that the first nine amino acids of human Syk are the same as those in porcine Syk. These same nine amino acids are present in the "guessmer", Syk ATG 2, used to determine the sequence of the NH$_2$ terminal SH2 domain of human Syk. Therefore, the partial 5' cDNA in Bluescript KS ATG 2/ASX possesses an intact open reading frame for the first 93 amino acids of human Syk, even though the sequence of the first nine amino acids was "forced" onto the cDNA during PCR amplification.

In order to generate a cDNA spanning the entire protein coding sequence of the syk gene, it was necessary to isolate a λ gt10 phage cDNA done from the Daudi cell library that contained the most 5' sequence of the gene and link it to the PCR generated syk 5' end done. To find such a cDNA 44 plaques positive for hybridization to the syk kinase domain (16 secondary, 28 primaries) were screened further by PCR amplification of phage supernatants with λ left and λ right primers, duplicate southern blotting of resultant products, and probing with either the human syk kinase domain probe under conditions described in (Church, G. M. and Gilbert, W., *Proc. Natl. Acad. Sci. USA,* 81:1991–1995 (1984), or with the Probe T from the N terminal SH2 domain of human Syk (hybridization in oligo hyb mix at 60° C.; washing in 2×SSC/1% SDS at 65° C.). Initially a single clone was positive for hybridization with the N terminal oligo probe but upon secondary screening with this probe, two different clones were actually pulled out. The insert that extended most 5 prime, from λ clone D5.1, was subcloned into Bluescript KS+ as an Eco RI fragment and its ends sequenced. From the sequence analysis it was determined that the D5.1 cDNA extended 5' to the $G_{67}$ residue of the Syk protein. It also became apparent that the D5.1 cDNA had arisen as a consequence of random priming, rather than oligo-dT priming, since the 3' end of the clone terminated at the $L_{560}$ residue. Hence it became necessary to supplement the 3' end of the D5.1 fragment with 3' syk sequence form an oligo-dT primed λ clone in addition to the 5' syk sequence from the PCR fragment.

A contiguous human syk cDNA was assembled into Bluescript SK- via a three-part ligation (FIG. 2) using the internal Ban I (nucleotide 198) and Bgl II (nucleotide 1464) sites of syk and the flanking (5') Xho I/(3') Eco RI sites from partial cDNAs (FIG. 2). The 5' PCR cDNA clone, Bluescript KS ATG2/AS X, was Ban I/BamHI digested, and the 200 bp fragment resolved on a low melt agarose gel. Similarly, the plasmid harboring "middle" syk cDNA fragment, D5/1 was Ban I/Bgl II digested, while the 3' end of the syk gene from the λ clone T11.1 was linearized with XhoI and Bgl II. All three fragments were mixed in a ligation and transformed into competent bacteria. Analysis of miniprep DNA identified a plasmid with the predicted restriction endonuclease sites. This plasmid, termed pBS-SK(−) hu syk, was subjected to complete DNA sequence analysis to confirm that it had the correct open reading frame of 630 codons for human syk.

EXAMPLE 2

Biospecific Interaction Analysis (BIA) In Real Time

Surface plasmon resonance (SPR), which is the basis for measurements with the BIAcore instrument (Pharmacia, Biosensor AB), is an optical phenomenon arising in thin metal films under conditions of total internal reflection.

This system provides a reliable and reproducible method for the estimation of kinetic parameters. Binding is measured in real time under accurately controlled conditions, such as temperature and flow rate. Moreover, there is no need for radiolabelling of one of the components and it is not necessary to devise methods for separation of bound from unbound ligand which invariably require a certain amount of time and may thus compromise the accurate measurement of kinetic parameters. One of the interacting molecules is immobilized on a dextran layer, which is in turn mounted on a gold surface. A monochromatic wedge of light is shone on this surface at a particular angle resulting in total deflection. Due to SPR, however, one component of the light, termed the evanescent wave, interacts with the electrons on the gold surface, resulting in a dip in the intensity of the reflected light. The angle at which this dip is observed (resonance angle) changes with the refractive index of the medium, which in turn relates to the mass concentration very dose to the gold surface. The resonance angle is measured by the instrument and converted to a plot of resonance units (RU) vs. time. The higher the RU value, the higher the amount of protein at the dextran matrix. This plot is called a sensogram. The presence of compounds different from those of the running buffer results in significant "bulk effects" being measured by the BIAcore instrument, which may distort the initial phase of the association and dissociation curves. Therefore, all protein solutions are passed through a desalting column equilibrated in BIAcore running buffer in order to achieve buffer exchange.

Estimation of kinetic parameters requires the repetitive injection of a range of protein concentrations over the immobilized capturing molecule. In order to be ready for a subsequent injection, the biosensor surface has to be regenerated at the end of each cycle so that any non-covalently bound protein will be removed. The tyrosine-phosphorylated peptides can be used as capturing molecules, as they are not affected by relatively harsh conditions, such as injection of SDS solutions. However, the direct covalent coupling of phosphopeptides to the dextran matrix may not be sufficient for accurate results because these small molecules may not be exposed enough to interact with the injected SH2 domains. Therefore, the biotin-avidin interaction principle can be used to place a long "spacer" between the phosphopeptides and the matrix. Avidin can be covalently immobilized on the matrix and then a biotinylated phosphopeptide solution is injected. Biotinylation of the phosphopeptides can be performed using NHS biotin according to standard laboratory techniques, resulting in the covalent attachment of biotin molecules at free amino groups on the peptide. Analysis of the biotinylation mixture can be performed by reverse-phase HPLC to reveal the peaks, representing varying degrees of biotinylation since both amino termini and lysine groups can be labelled. Mass analysis can also be used to identify the number of biotin molecules attached and the peaks corresponding to one biotin per peptide are used for subsequent interactions.

Association and dissociation rate constants can be calculated by repetitive injections of increasing concentrations of protein over immobilized phosphopeptides, as described in the BIAcore Methods Manual. The binding of a peptide to an SH2 domain of a protein kinase is described below.

Binding of the N-SH2 peptide of PI3K p85 to pY.V.P.M.L. a PI3K ligand (SEQ ID NO: 31) was synthesized as part of a larger peptide (SEQ ID NO: 32) and immobilized to the biosensor surface via the C-terminal lysine using standard EDC/NHS chemistry. To determine the binding affinity (Ka) of the N-terminal SH2 peptide of the PI3K p85 for the immobilized phosphopeptide, the on rates, off rates and steady state binding characteristics for several different concentrations of SH2 peptide (0.5, 0.67, 1.0, 2.0 and 4.0 uM) were measured from changes in the surface plasmon resonance elicited by ligand/ protein interaction. The Ka for the above interaction was determined to be 160 nM.

EXAMPLE 3

Mast Cell/Basophil Degranulation Assays

A. Intact Cell Assays

The release of β-hexosaminidase from basophils is measured as an in vitro assay of basophil activation. A cell line, RBL-2H3 (from the laboratory of Dr. Siraganian, National Institutes of Health), of rat basophil leukemia (RBL) cells is used in such an in vitro assay, according to the protocol described below (Barsumian et al., Eur. J. Immunol. 11:317–323 (1981)). The percentage of β-hexosaminidase in cells that is released into the cell medium is determined, and is a measure of the activation of the RBL-2H3 cells.

ACTIVATION OF 2BL-2H3 CELLS

MATERIALS

RBL medium containing 2% fetal bovine serum (FBS)
  100 ml E-MEM
  2 ml FBS
  1 ml FBS
  1.2 ml penicillin-streptomycin
filter sterilize into sterile bottles or tissue culture flasks and store at 4° C.

10×PIPES buffer
  75.6 g PIPES (0.25 M)
  69.2 g NaCl (1.2 M)
  3.72 g KCl (0.05 M)
  43 ml of 10 N NaOH (0.4 M)
  Add water to 1000 ml
filter sterilize into sterile bottles or tissue culture flasks and store at 4° C.

100×calcium chloride
  1.47 g $CaCl_2 \cdot 2H_2O$ (100 mM)
  Add water to 100 ml
filter sterilize into sterile bottles or tissue culture flasks and store at 4° C.

2×-IgE (anti DNP-IgE mouse monoclonal antibody; Zymed) in regular RBL medium containing 15% FBS
Need 0.5 ml at 2-times an appropriate final dilution for each 16 mm well to be seeded with cells 1×PIPES+glucose+calcium (prepare fresh on second day of assay)
  10 ml of 10×PIPES
  0.1 g glucose (dextrose) (5.6 Mm)
  0.1 g bovine serum albumin (BSA)
  1 ml of 100×calcium chloride
Add water to 90 ml; pH to 7.4; milli-Q water to 100 ml

METHOD

Remove RBL cells from flasks by trypsin-EDTA treatment (see protocol infra). Plan to use $1 \times 10^5$ cells/16 mm well to be seeded; harvest extra cells to allow for losses during centrifugation.

Centrifuge the RBL cells and resuspend in 5 ml of regular RBL medium containing 15% FBS. Count the cells and dilute them to $2 \times 10^5$ cells/ml in the same medium.

For each well to be seeded, mix 0.5 ml of cells with 0.5 ml of 2×-IgE.

Seed 1 ml of Ige-RBL per 16 mm well.

Incubate plate(s) overnight at 37° C./5% $CO_2$.

Next day, dilute the DNP-HSA (dinitrophenol-human serum albumin; Calbiochem) to an appropriate dilution in 1×PIPES+glucose+calcium; 0.5 ml will be needed for each well.

Remove the plate(s) from the incubator and aspirate the media from the wells.

Add 2 ml of 1×PIPES+glucose+calcium to each well and aspirate again.

Repeat the last step.

Add the 0.5 ml of diluted DNP-BSA (or 1×PIPES+glucose+calcium alone as the negative control in triplicate) to wells.

Incubate 40 min at 37° C./5% $CO_2$.

Meanwhile, label 12×75 tubes (round or conical bottom) to receive each supernatant and the cells themselves from the triplicate negative controls; also label 12×75 tubes for the beta-hexosaminidase assay.

After the incubation, carefully transfer each supernatant from the 16 mm wells to appropriate tubes on ice.

Add 250 µl of enzyme-free cell dissociation solution (Enzyme Free Cell Dissociation Solution Hank's Balanced Salts Based Formulation, Specialty Media Inc., Lavallette, N.J.) to each of the triplicate negative control wells and incubate 5 min at 37° C.

Transfer the 250 µl aliquots to conical bottom centrifuge tubes. Add 250 µl of PIPES+glucose+calcium to rinse each well and transfer to the appropriate tubes.

Spin tubes 5 min at 1000 rpm and remove supernatants. Resuspend each in 500 µl of PIPES+glucose+calcium.

Sonicate cell suspensions on ice (5 pulses); if no probe sonifier is available, freeze thaw cells 3×using a methanol or ethanol-dry ice bath and a 37° C. water bath.

Transfer 100 µl of each supernatant or cell lysate to a 12×75 tube and proceed with the beta-hexosaminidase ("beta-hex") assay protocol.

Protocol for Removing RBL Cells from Flasks

Prepare trypsin/EDTA by diluting stock 1:10 in HBSS—; filter sterilize.

Aspirate the medium from a flask of cells.

Add 10 ml of HBSS—and gently rinse the flask.

Aspirate the HBSS—.

Add 3 ml of trypsin/EDTA and incubate 5 min at 37° C.

Rap the flask several times to loosen the cells.

Transfer the 3 ml to a tube.

Rinse flask with 10 ml of the above medium and pool to the tube.

BETA-HEXOSAMINIDASE ASSAY
MATERIALS
1. Beta-hex buffer

Solution 1: 0.2 M $Na_2PO_4$ (sodium phosphate dibasic ANHYDROUS)—14.2 g/500 ml distilled $H_2O$
NOTE: If there is no anhydrous, use the sodium phosphate dibasic
HEPTAHYDRATE ($7H_2O$), but use 26.7 grams.

Solution 2: 0.4 M citric acid monohydrate—42.1 g/500 ml distilled $H_2O$

Mix approximately 70 ml of solution with approximately 20 ml solution 2 until the pH is 4.5 (use solution 1 to raise the pH and solution 2 to lower it)

2. Beta-hex cocktail

Beta-hex buffer (from above): 90 ml
Distilled $H_2O$: 135 ml
p-nitrophenyl-N-acetyl-beta-D-glucosaminide (p-nitrophenyl-beta-D-2-acetamide-2-deoxy-beta-D-glucopyranoside) (Sigma N-9376): 300 mg
(0.30 g); stored at −20° C.
Mix until dissolved Aliquot in 15 ml tubes, label, date, and freeze at −20° C.

3. Beta-hex STOP solution
glycine: 15.0 g/liter bring to pH 10.7 with N NaOH (will need to add ~30 ml of NaOH)

METHOD

1. Place 100 µl of sample in each 12×75 polystyrene round-bottom tube.
2. Add 40 µl of beta-hex cocktail to each tube.
3. Cover with tin foil and incubate tubes 30 min at 37° C.
4. Add 1.5 ml of beta-hex stop to each tube.
5. Turn on the spectrophotometer and allow it to warm up 10 minutes.
6. Turn on the vacuum pump attached to the spectrophotometer.
7. Set the wavelength for 410 nm.
8. Aspirate any liquid in the spectrophotometer tubing.
9. Zero the spectrophotometer using beta-hex stop solution.
10. Aspirate liquid from the tubing; double check reading with more beta-hex stop.
11. Aspirate the liquid from the tubing; read the absorbance at 410 nm (A410) of each sample within one hour, remembering to aspirate the sample from the tubing between each one.

CALCULATION OF RESULTS

Determine the total beta-hex present in the RBL cells by adding the supernatant (S) and cell lysate (C) values for each of the triplicate negative controls and determine the mean [S+C].

Determine the % release for each supernatant by taking the beta-hex value and dividing by (S+C)×100.

Determine the net % release by subtracting the % release value for the control from each % release value where DNP-BSA was added.

B. PERMEABILIZED CELL ASSAYS

The mast cell/basophil degranulation assay can also be performed using permeabilized cells, according to the protocol described below (Cunha-Melo et al., *J. Immunol.* 143:2617–2625 (1989); Ali et al., *J. Immunol.* 143:2626–2633 (1989); Ali et al., *Biochim. Biophys. Acta* 1010:88–99 (1989)).

PROTOCOL FOR PERMEABILIZATION OF RBL-2H3 CELLS WITH STREPTOLYSIN O (1) Buffer:

| | |
|---|---|
| Potassium glutamate | 138.7 mM |
| Glucose | 5 mM |
| Potassium salt of PIPES | 20 mM |
| Magnesium Acetate | 7 mM |

Make 1 liter of the above buffer, do not adjust pH, sterile filter and store at 4° until use.

At the time of use, remove appropriate volume and add the following:

1 M EGTA to give final concentration of 1 mM.
ATP (Sigma #A2383) to a final concentration of 5 mM.
Add $CaCl_2$ (1 M) to a final concentration of 0.213 mM.
In the presence of 1 mM EGTA the free $[Ca^{2+}]$ is 100 nM.
Adjust pH to 7.0.
BSA (1 mg/ml) optional.
LiCl (10 to 20 nM) for phosphoinositide hydrolysis experiments.

(2) Streptolysin O

Streptolysin O reduced (Burrough's Wellcome; catalog #MR 16).

Add 4 ml $H_2O$ to 40 I.U. of streptolysin O. (10 units/ml). Make aliquots and freeze immediately.

(3) Permeabilization

RBL-2H3 cells ($0.3×10^6$/well, in growth medium) are plated in 24 well tissue culture plate and incubated overnight.

The following day, cells are washed twice with potassium glutamate (KG) buffer (500 µl).

The cells are permeabilized by exposure to streptolysin O (0.1 to 0.3 units/ml, 200–500 µl/well) for 5 to 10 min. The concentration of streptolysin O and the time required for permeabilization depends on the number of passages the cells have been cultured for and may vary with batch of streptolysin O. A useful starting point is to permeabilize cells with 0.25 I.U./ml streptolysin for 10 min.

Streptolysin O solution is prepared just before permeabilization by dilution of the stock solution (10 I.U./ml) into prewarmed KG buffer.

After the cells are permeabilized, remove buffer by aspiration, add fresh buffer (without toxin) and perform experiment as desired to measure cell activation (e.g., measure phosphoinositide hydrolysis, or β-hexosaminidase or histamine release). Modifications of the permeabilization procedure can be made for measuring degranulation.

EXAMPLE 4

Overexpression and Purification of the C-terminal SH2 domain of Human Syk

The sequence encoding the amino acids 163 to 265 (SEQ ID NO: 33) was amplified by the polymerase chain reaction using Taq polymerase (BMB) and oligonucleotide primers (SEQ ID NOS: 34 and 35) from the plasmid termed pBS-SK(−) hu syk. After digestion with the restriction endonucleases BamH1 (5') and EcoR1 (3'), the gel purified fragment was subcloned into the expression vector pGEX2TK using T4 ligase (BMB) to product the plasmid pGEX2TKCSyk(+11). The sequence of the C-terminal SH2 was determined using the chain-termination methods as described in the Sequenase (US Biochemical) protocols.

A 2 liter culture (LB medium, 100 ug/ml ampicillin) of pGEXCSyk(+11) in transformed *E. coli* BL21(DE3) (Novagen) was grown at 37° C. to an $OD_{595}$ of 0.432, induced with 1 mM isopropyl b-D-thiogalactopyranoside (IPTG), shifted to 25 ° C. and harvested 12 hours later. After resuspension in phosphate buffered saline (PBS)/0.5% Triton X-100, the cells were lysed by two passes in a French Pressure Cell at 16,000 psi. After centrifugation at 7000×g for 20 minutes, the supernatant was purified by affinity chromatography with glutathione resin followed by elution with 20 mM glutathione in 100 mM Tris pH 8.0/100 nM NaCl. This procedure yielded 25 mg/L purified fusion protein as determined by SDS-polyacrylamide gel electrophoresis.

EXAMPLE 5

In Vitro Transcription/Translation Assay

OBJECTIVE

The purpose of this assay is two fold, to determine if the following SH2 domains are functional via binding to phosphotyrosine and to develop an assay to screen and identify ligand targets (peptide or mimetics) which bind to these SH2 domains.

PROTOCOL

1. The SH2 domain constructs can be subcloned into pCITE (Novagen) which has a cap-independent translation enhancer and the His-tag sequence as a C-terminal fusion allowing for the purification of the full translation product if needed. This vector has been designed for increased translation (use of 110 mM KCl during translation increases the translation yield 10 fold over uncapped transcripts).
2. The in vitro transcription can be done on each construct. The RNA is prepared using the in vitro transcription kit from Novagen.
3. The in vitro translation can be carried out using the Red Nova lysate (Novagen) using the minus leucine or minus methionine Red Nova lysate kit (for the domains that have very few to no methionines the translation can be done using H-3 leucine).
4. Aliquots of the translation products can be analyzed by autoradiography on an 15–20% SDS-PAGE gel. Protein concentration can be determined using routine laboratory methods.
5. The full translation product can be purified using His-tag/Ni resin if there is a mixture of products as determined by the autoradiograph. The protein can be eluted with imidazole.
6. The labeled ($H^3$ Leu or $^{35}$S Met) SH2 translation product can be incubated with the phosphotyrosine-sepharose beads (Sigma) for 30 minutes. The protein-bound beads are then washed (3 times) and an aliquot counted. The protein bound to the phosphotyrosine can either be used in competition assays or eluted with phenyl phosphate for direct binding assays as described below.

ASSAYS

Competition for the Phosphotyrosine Binding:

Competition experiments can also be performed using nonbiotinylated peptides or peptide mimetics to compete off the phosphotyrosine (determine IC50 for the peptide). The affinity purified (via phosphotyrosine) S-35 or H-3 labeled SH2 domains which are still bound to phosphotyrosine beads are incubated with the peptide (PDGF-R, TAM, etc.) or peptide mimetic. The sample is washed (3×), and counted. The $IC_{50}$ for different peptides (i.e., the concentration of peptide that elutes 50% of the labeled SH2 domain) is then determined.

Direct Binding:

The affinity purified (via phosphotyrosine) $^{35}$S or H-3 labeled SH2 domains (eluted from the phosphotyrosine beads) are incubated with a peptide (e.g., TAM) and then precipitated with strepavidin-agarose beads (Pierce), washed (3×) and counted. This direct binding interaction can be quantitated by counting the ligand bound $^{35}$S or H-3 labeled protein.

Model System

The model system for the in vitro transcription/translation assay will be the lyn SH2 with the peptide KGGQY$^P$EEIPI and the N-terminal domain of PI3K with the NAcY$^P$VPM-LGGK. Both protein SH2 domains can be ligated easily into the vector at the NdeI-5'/BamHI-3' sites. The peptide Y$^P$VP-MLGGK (without the N-Ac) has been biotinylated and purified. Variations of this peptide as well as variations of the PDGF-R have been made available to me (J. Green) for competition studies.

These constructs will be used as the model system to develop the assay. The following nonfusion SH2 domain constructs are being subcloned into pCITE using the NdeI (5') and BamHI (3') restriction sites: lyn (U+SH3+SH2), lyn SH2 (+5 AA), PI3K NSH2.

The following N-terminal and C-terminal SH2 domains of Syk will also be cloned into the NdeI (5') and BamHI (3') using the restriction sites [NSyk M(+9) & G (+5) will be subcloned via the BamHI (5') and EcoR1 (3')] and tested with the phosphorylated FceRI-_peptides. These phosphorylated peptides have been made available to me (Y. Green). These experiments can be performed as competition experiments, by competing for the phosphotyrosine-protein interaction or biotinylated and done as a direct binding assay using the strepavidin beads.

NSyk (F, N-terminus)
NSyk (+9 AA & +5 AA, M on the N-terminus and G on the C-terminus)
CSyk (+5 AA, H on the N-terminus)
CSyk (+5 AA & +12 AA, H on the N-terminus and G on the C-terminus)

EQUIVALENTS

Those skilled in the art will recognize, or be able to ascertain using no more than routine experimentation, many equivalents to be specific embodiments of the invention described herein. Such equivalents are intended to be encompassed by the following claims.

The invention claimed is:

1. An isolated nucleic acid comprising a coding sequence encoding the amino acid sequence spanning positions Met-1 through Gly-180 of SEQ ID NO:2, or naturally occurring human allelic variants thereof.

2. An isolated nucleic acid comprising the nucleotide sequence spanning positions A-1 through A-540 of SEQ ID NO: 1, or naturally occurring human allelic variants thereof.

3. An isolated nucleic acid comprising the nucleotide sequence spanning positions A-1 through C-1890 of SEQ ID NO: 1, or naturally occurring human allelic variants thereof.

4. A recombinant DNA construct comprising a nucleic acid of claims 1, 2 or 3, and heterologous DNA.

5. A genetically engineered host cell containing a recombinant DNA construct of claim 4.

6. An isolated nucleic acid comprising a coding sequence for a naturally occurring human SYK protein, or at least an SH2 domain thereof, which coding sequence hybridizes under stringent conditions of 2×SSC/1% SDS at 65° C. to SEQ ID No. 1.

7. The nucleic acid of claim 6, wherein the protein further includes a kinase domain of the human SYK protein.

8. An isolated nucleic acid comprising a coding sequence for a naturally occuring human SYK protein, or at least the kinase domain thereof.

9. The nucleic acid of claim 8, comprising a coding sequence for the SYK protein of SEQ ID NO:2, or at least the kinase domain thereof.

10. The nucleic acid of claim 8, comprising a coding sequence for the full length SYK protein of SEQ ID NO:2.

11. An isolated nucleic acid comprising the coding sequence of SEQ ID NO:1, or portion thereof encoding at least a kinase domain.

12. The nucleic acid of claim 9, comprising the full-length coding sequence of SEQ ID NO:1.

13. An isolated nucleic acid comprising: (i) a coding sequence for a naturally occuring human SYK protein, or at least an SH2 domain thereof, which coding sequence hybridizes under stringent conditions of 2×SSC/1% SDS at 65° C. to SEQ ID No. 1; and (ii) a transcriptional regulatory sequence operably linked thereto.

14. The nucleic acid of claim 13, wherein the coding sequence is the coding sequence of SEQ ID NO:1, or a portion thereof encoding at least a kinase domain.

15. The nucleic acid of claim 13, wherein the coding sequence encodes the SYK protein of SEQ ID NO:2, or at least the kinase domain.

16. An isolated nucleic acid comprising: (i) a coding sequence for the SYK protein of SEQ ID NO:2, and (ii) a transcriptional regulatory sequence operably linked thereto.

17. A genetically engineered host cell containing the nucleic acid of any of claims 6, 7, 8, 9, 10, 11, 12, 13, 14, 15 or 16.

* * * * *

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
    (A) LENGTH: 1893 base pairs
    (B) TYPE: nucleic acid
    (C) STRANDEDNESS: double
    (D) TOPOLOGY: linear (ii) MOLECULE TYPE: cDNA (ix) FEATURE:
    (A) NAME/KEY: CDS
    (B) LOCATION: 1..1890

(ix) FEATURE:
    (A) NAME/KEY: N-SH2 DOMAIN
    (B) LOCATION: 28-306

(ix) FEATURE:
    (A) NAME/KEY: C-SH2 DOMAIN
    (B) LOCATION: 487-762

(ix) FEATURE:
    (A) NAME/KEY: KINASE DOMAIN
    (B) LOCATION: 1096-1893

(xi) SEQUENCE DESCRIPTION: SEQ ID NO:1:

```
ATG GCA GAC AGC GCG AAC CAC TTG CCC TTC TTT TTC GGC AAC ATC ACC        48
Met Ala Asp Ser Ala Asn His Leu Pro Phe Phe Phe Gly Asn Ile Thr
 1               5                  10                  15

CGG GAG GAG GCA GAA GAT TAC CTG GTC CAG GGG GGC ATG AGT GAT GGG        96
Arg Glu Glu Ala Glu Asp Tyr Leu Val Gln Gly Gly Met Ser Asp Gly
                20                  25                  30

CTT TAT TTG CTG CGC CAG AGC CGC AAC TAC CTG GGT GGC TTC GCC CTG       144
Leu Tyr Leu Leu Arg Gln Ser Arg Asn Tyr Leu Gly Gly Phe Ala Leu
         35                  40                  45

TCC GTG GCC CAC GGG AGG AAG GCA CAC CAC TAC ACC ATC GAG CGG GAG       192
Ser Val Ala His Gly Arg Lys Ala His His Tyr Thr Ile Glu Arg Glu
 50                  55                  60

CTG AAT GGC ACC TAC GCC ATC GCC GGT GGC AGG ACC CAT GCC AGC CCC       240
Leu Asn Gly Thr Tyr Ala Ile Ala Gly Gly Arg Thr His Ala Ser Pro
 65                  70                  75                  80

GCC GAC CTC TGC CAC TAC CAC TCC CAG GAG TCT GAT GGC CTG GTC TGC       288
Ala Asp Leu Cys His Tyr His Ser Gln Glu Ser Asp Gly Leu Val Cys
                 85                  90                  95

CTC CTC AAG AAG CCC TTC AAC CGG CCC AAG GGG TGC AGC CCG AAG ACT       336
Leu Leu Lys Lys Pro Phe Asn Arg Pro Lys Gly Cys Ser Pro Lys Thr
            100                 105                 110

GGG CCC TTT GAG GAT TTG AAG GAA AAC CTC ATC AGG GAA TAT GTG AAG       384
Gly Pro Phe Glu Asp Leu Lys Glu Asn Leu Ile Arg Glu Tyr Val Lys
        115                 120                 125

CAG ACA TGG AAC CTG CAG GGT CAG GCT CTG GAG CAG GCC ATC ATC AGT       432
Gln Thr Trp Asn Leu Gln Gly Gln Ala Leu Glu Gln Ala Ile Ile Ser
    130                 135                 140

CAG AAG CCT CAG CTG GAG AAG CTG ATC GCT ACC ACA GCC CAT GAA AAA       480
Gln Lys Pro Gln Leu Glu Lys Leu Ile Ala Thr Thr Ala His Glu Lys
145                 150                 155                 160

ATG CCT TGG TTC CAT GGA AAA ATC TCT CGG GAA GAA TCT GAG CAA ATT       528
Met Pro Trp Phe His Gly Lys Ile Ser Arg Glu Glu Ser Glu Gln Ile
                165                 170                 175
```

| | |
|---|---|
| GTC CTG ATA GGA TCA AAG ACA AAT GGA AAG TTC CTG ATC CGA GCC AGA<br>Val Leu Ile Gly Ser Lys Thr Asn Gly Lys Phe Leu Ile Arg Ala Arg<br>180 185 190 | 576 |
| GAC AAC AAC GGC TCC TAC GCC CTG TGC CTG CTG CAC GAA GGG AAG GTG<br>Asp Asn Asn Gly Ser Tyr Ala Leu Cys Leu Leu His Glu Gly Lys Val<br>195 200 205 | 624 |
| CTG CAC TAT CGC ATC GAC AAA GAC AAG ACA GGG AAG CTC TCC ATC CCC<br>Leu His Tyr Arg Ile Asp Lys Asp Lys Thr Gly Lys Leu Ser Ile Pro<br>210 215 220 | 672 |
| GAG GGA AAG AAG TTC GAC ACG CTC TGG CAG CTA GTC GAG CAT TAT TCT<br>Glu Gly Lys Lys Phe Asp Thr Leu Trp Gln Leu Val Glu His Tyr Ser<br>225 230 235 240 | 720 |
| TAT AAA GCA GAT GGT TTG TTA AGA GTT CTT ACT GTC CCA TGT CAA AAA<br>Tyr Lys Ala Asp Gly Leu Leu Arg Val Leu Thr Val Pro Cys Gln Lys<br>245 250 255 | 768 |
| ATC GGC ACA CAG GGA AAT GTT AAT TTT GGA GGC CGT CCA CAA CTT CCA<br>Ile Gly Thr Gln Gly Asn Val Asn Phe Gly Gly Arg Pro Gln Leu Pro<br>260 265 270 | 816 |
| GGT TCC CAT CCT GCG ACT TGG TCA GCG GGT GGA ATA ATC TCA AGA ATC<br>Gly Ser His Pro Ala Thr Trp Ser Ala Gly Gly Ile Ile Ser Arg Ile<br>275 280 285 | 864 |
| AAA TCA TAC TCC TTC CCA AAG CCT GGC CAC AGA AAG TCC TCC CCT GCC<br>Lys Ser Tyr Ser Phe Pro Lys Pro Gly His Arg Lys Ser Ser Pro Ala<br>290 295 300 | 912 |
| CAA GGG AAC CGG CAA GAG AGT ACT GTG TCA TTC AAT CCG TAT GAG CCA<br>Gln Gly Asn Arg Gln Glu Ser Thr Val Ser Phe Asn Pro Tyr Glu Pro<br>305 310 315 320 | 960 |
| GAA CTT GCA CCC TGG GCT GCA GAC AAA GGC CCC CAG AGA GAA GCC CTA<br>Glu Leu Ala Pro Trp Ala Ala Asp Lys Gly Pro Gln Arg Glu Ala Leu<br>325 330 335 | 1008 |
| CCC ATG GAC ACA GAG GTG TAC GAG AGC CCC TAC GCG GAC CYC GAG GAG<br>Pro Met Asp Thr Glu Val Tyr Glu Ser Pro Tyr Ala Asp Pro Glu Glu<br>340 345 350 | 1056 |
| ATC AGG CCC AAG GAG GTT TAC CTG GAC CGA AAG CTG CTG ACG CTG GAA<br>Ile Arg Pro Lys Glu Val Tyr Leu Asp Arg Lys Leu Leu Thr Leu Glu<br>355 360 365 | 1104 |
| GAC AAA GAA CTG GGC TCT GGT AAT TTT GGA ACT GTG AAA AAG GGC TAC<br>Asp Lys Glu Leu Gly Ser Gly Asn Phe Gly Thr Val Lys Lys Gly Tyr<br>370 375 380 | 1152 |
| TAC CAA ATG AAA AAA GTT GTG AAA ACC GTG GCT GTG AAA ATA CTG AAA<br>Tyr Gln Met Lys Lys Val Val Lys Thr Val Ala Val Lys Ile Leu Lys<br>385 390 395 400 | 1200 |
| AAC GAG GCC AAT GAC CCC GCT CTT AAA GAT GAG TTA TTA GCA GAA GCA<br>Asn Glu Ala Asn Asp Pro Ala Leu Lys Asp Glu Leu Leu Ala Glu Ala<br>405 410 415 | 1248 |
| AAT GTC ATG CAG CAG CTG GAC AAC CCG TAC ATC GTG CGR ATG ATC GGG<br>Asn Val Met Gln Gln Leu Asp Asn Pro Tyr Ile Val Arg Met Ile Gly<br>420 425 430 | 1296 |
| ATA TGC GAG GCC GAG TCC TGG ATG CTR GTT ATG GAG ATG GCA GAA CTT<br>Ile Cys Glu Ala Glu Ser Trp Met Leu Val Met Glu Met Ala Glu Leu<br>435 440 445 | 1344 |
| GGT CCC CTC AAT AAG TAT TTG CAG CAG AAC AGA CAT GTC AAG GAT AAG<br>Gly Pro Leu Asn Lys Tyr Leu Gln Gln Asn Arg His Val Lys Asp Lys<br>450 455 460 | 1392 |
| AAC ATC ATA GAA CTG GTT CAT CAG GTT TCC ATG GGC ATG AAG TAC TTG<br>Asn Ile Ile Glu Leu Val His Gln Val Ser Met Gly Met Lys Tyr Leu<br>465 470 475 480 | 1440 |
| GAG GAG AGC AAT TTT GTG CAC AGA GAT CTG GCT GCA AGA AAT GTG TTG<br>Glu Glu Ser Asn Phe Val His Arg Asp Leu Ala Ala Arg Asn Val Leu<br>485 490 495 | 1488 |

-continued

```
CTA GTT ACC CAA CAT TAC GCC AAG ATC AGT GAT TTC GGA CTT TCC AAA         1536
Leu Val Thr Gln His Tyr Ala Lys Ile Ser Asp Phe Gly Leu Ser Lys
        500                 505                 510

GCA CTG CGT GCT GAT GAA AAC TAC TAC AAG GCC CAG ACC CAT GGA AAG         1584
Ala Leu Arg Ala Asp Glu Asn Tyr Tyr Lys Ala Gln Thr His Gly Lys
        515                 520                 525

TGG CCT GTC AAG TGG TAC GCT CCG GAA TGC ATC AAC TAC TAC AAG TTC         1632
Trp Pro Val Lys Trp Tyr Ala Pro Glu Cys Ile Asn Tyr Tyr Lys Phe
530                 535                 540

TCC AGC AAA AGC GAT GTC TGG AGC TTT GGA GTG TTG ATG TGG GAA GCA         1680
Ser Ser Lys Ser Asp Val Trp Ser Phe Gly Val Leu Met Trp Glu Ala
545                 550                 555                 560

TTC TCC TAT GGG CAG AAG CCA TAT CGA GGG ATG AAA GGA AGT GAA GTC         1728
Phe Ser Tyr Gly Gln Lys Pro Tyr Arg Gly Met Lys Gly Ser Glu Val
            565                 570                 575

ACC GCT ATG TTA GAG AAA GGA GAG CGG ATG GGG TGC CCT GCA GGG TGT         1776
Thr Ala Met Leu Glu Lys Gly Glu Arg Met Gly Cys Pro Ala Gly Cys
        580                 585                 590

CCA AGA GAG ATG TAC GAT CTC ATG AAT CTG TGC TGG ACA TAC GAT GTG         1824
Pro Arg Glu Met Tyr Asp Leu Met Asn Leu Cys Trp Thr Tyr Asp Val
        595                 600                 605

GAA AAC AGG CCC GGA TTC GCA GCA GTG GAA CTG CGG CTG CGC AAT TAC         1872
Glu Asn Arg Pro Gly Phe Ala Ala Val Glu Leu Arg Leu Arg Asn Tyr
610                 615                 620

TAC TAT GAC GTG GTG AAC TAA                                             1893
Tyr Tyr Asp Val Val Asn
625                 630
```

(2) INFORMATION FOR SEQ ID NO:2:

(i) SEQUENCE CHARACTERISTICS:
        (A) LENGTH: 630 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Asp Ser Ala Asn His Leu Pro Phe Phe Gly Asn Ile Thr
 1               5                  10                  15

Arg Glu Glu Ala Glu Asp Tyr Leu Val Gln Gly Gly Met Ser Asp Gly
                20                  25                  30

Leu Tyr Leu Leu Arg Gln Ser Arg Asn Tyr Leu Gly Gly Phe Ala Leu
        35                  40                  45

Ser Val Ala His Gly Arg Lys Ala His His Tyr Thr Ile Glu Arg Glu
    50                  55                  60

Leu Asn Gly Thr Tyr Ala Ile Ala Gly Gly Arg Thr His Ala Ser Pro
65                  70                  75                  80

Ala Asp Leu Cys His Tyr His Ser Gln Glu Ser Asp Gly Leu Val Cys
                85                  90                  95

Leu Leu Lys Lys Pro Phe Asn Arg Pro Lys Gly Cys Ser Pro Lys Thr
            100                 105                 110

Gly Pro Phe Glu Asp Leu Lys Glu Asn Leu Ile Arg Glu Tyr Val Lys
        115                 120                 125

Gln Thr Trp Asn Leu Gln Gly Gln Ala Leu Glu Gln Ala Ile Ile Ser
    130                 135                 140

Gln Lys Pro Gln Leu Glu Lys Leu Ile Ala Thr Thr Ala His Glu Lys
145                 150                 155                 160

Met Pro Trp Phe His Gly Lys Ile Ser Arg Glu Glu Ser Glu Gln Ile
                165                 170                 175
```

```
Val Leu Ile Gly Ser Lys Thr Asn Gly Lys Phe Leu Ile Arg Ala Arg
            180                 185                 190

Asp Asn Asn Gly Ser Tyr Ala Leu Cys Leu Leu His Glu Gly Lys Val
            195                 200                 205

Leu His Tyr Arg Ile Asp Lys Asp Lys Thr Gly Lys Leu Ser Ile Pro
            210                 215                 220

Glu Gly Lys Lys Phe Asp Thr Leu Trp Gln Leu Val Glu His Tyr Ser
225                 230                 235                 240

Tyr Lys Ala Asp Gly Leu Leu Arg Val Leu Thr Val Pro Cys Gln Lys
            245                 250                 255

Ile Gly Thr Gln Gly Asn Val Asn Phe Gly Arg Pro Gln Leu Pro
            260                 265                 270

Gly Ser His Pro Ala Thr Trp Ser Ala Gly Ile Ile Ser Arg Ile
            275                 280                 285

Lys Ser Tyr Ser Phe Pro Lys Pro Gly His Arg Lys Ser Ser Pro Ala
            290                 295                 300

Gln Gly Asn Arg Gln Glu Ser Thr Val Ser Phe Asn Pro Tyr Glu Pro
305                 310                 315                 320

Glu Leu Ala Pro Trp Ala Ala Asp Lys Gly Pro Gln Arg Glu Ala Leu
            325                 330                 335

Pro Met Asp Thr Glu Val Tyr Glu Ser Pro Tyr Ala Asp Pro Glu Glu
            340                 345                 350

Ile Arg Pro Lys Glu Val Tyr Leu Asp Arg Lys Leu Leu Thr Leu Glu
            355                 360                 365

Asp Lys Glu Leu Gly Ser Gly Asn Phe Gly Thr Val Lys Lys Gly Tyr
            370                 375                 380

Tyr Gln Met Lys Lys Val Val Lys Thr Val Ala Val Lys Ile Leu Lys
385                 390                 395                 400

Asn Glu Ala Asn Asp Pro Ala Leu Lys Asp Glu Leu Leu Ala Glu Ala
            405                 410                 415

Asn Val Met Gln Gln Leu Asp Asn Pro Tyr Ile Val Arg Met Ile Gly
            420                 425                 430

Ile Cys Glu Ala Glu Ser Trp Met Leu Val Met Glu Met Ala Glu Leu
            435                 440                 445

Gly Pro Leu Asn Lys Tyr Leu Gln Gln Asn Arg His Val Lys Asp Lys
            450                 455                 460

Asn Ile Ile Glu Leu Val His Gln Val Ser Met Gly Met Lys Tyr Leu
465                 470                 475                 480

Glu Glu Ser Asn Phe Val His Arg Asp Leu Ala Ala Arg Asn Val Leu
            485                 490                 495

Leu Val Thr Gln His Tyr Ala Lys Ile Ser Asp Phe Gly Leu Ser Lys
            500                 505                 510

Ala Leu Arg Ala Asp Glu Asn Tyr Tyr Lys Ala Gln Thr His Gly Lys
            515                 520                 525

Trp Pro Val Lys Trp Tyr Ala Pro Glu Cys Ile Asn Tyr Tyr Lys Phe
            530                 535                 540

Ser Ser Lys Ser Asp Val Trp Ser Phe Gly Val Leu Met Trp Glu Ala
545                 550                 555                 560

Phe Ser Tyr Gly Gln Lys Pro Tyr Arg Gly Met Lys Gly Ser Glu Val
            565                 570                 575

Thr Ala Met Leu Glu Lys Gly Glu Arg Met Gly Cys Pro Ala Gly Cys
            580                 585                 590

Pro Arg Glu Met Tyr Asp Leu Met Asn Leu Cys Trp Thr Tyr Asp Val
```

```
                    595                 600                 605
Glu Asn Arg Pro Gly Phe Ala Ala Val Glu Leu Arg Leu Arg Asn Tyr
                610                 615                 620

Tyr Tyr Asp Val Val Asn
625                 630
```

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GGCTCGAGTT YTTYTTYGGN CARATTAC                      28

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GGCTCGAGTT YTTYTTYGGN CARATAAC                      28

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGCTCGAGTT YTTYTTYGGN CARATCAC                      28

(2) INFORMATION FOR SEQ ID NO:6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CCCATCGATC CRTGRAACCA NGGCATYTTT TC                  32

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
CCCATCGATC CRTGRAACCA NGGCATYTTC TC                              32
```

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
GGCTCGAGTG GATGCTDGTN ATGGAAATGG C                               31
```

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GGCTCGAGTG GATGCTDGTN ATGGAGATGG C                               31
```

(2) INFORMATION FOR SEQ ID NO:10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
CCCATCGATA RTCHACHACR TCRTARTART AGTT                            34
```

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
CCCATCGATA RTCHACHACR TCRTADARTA ATT                             33
```

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
AGTATTTGCA GCAGAACCAG A                                          21
```

(2) INFORMATION FOR SEQ ID NO:13:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

CCCATCGATA TGATGTTCTT ATCCTTGACA TG                                              32

(2) INFORMATION FOR SEQ ID NO:14:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

CATGGAAACC TGATGAACCA GTTC                                                      24

(2) INFORMATION FOR SEQ ID NO:15:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:15:

GACTGCTGGG TAGTCCCCAC CTTTT                                                     25

(2) INFORMATION FOR SEQ ID NO:16:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:16:

GAGCAAGTTC AGCCTGGTTA AGTCC                                                     25

(2) INFORMATION FOR SEQ ID NO:17:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:17:

GGGGTAAAAT AACAGAGGTG GCTTAT                                                    26

(2) INFORMATION FOR SEQ ID NO:18:

(i) SEQUENCE CHARACTERISTICS:
            (A) LENGTH: 25 base pairs
            (B) TYPE: nucleic acid
            (C) STRANDEDNESS: single (D) TOPOLOGY: linear (ii) MOLECULE TYPE: cDNA (xi) SEQUENCE DESCRIPTION: SEQ ID NO:18:

GAGTATTTCT TCCAGGGTAA AAAGC                                    25

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CAGCCCCGCC GACCTCTGCC A                                        21

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

CCCATCGATC CATCAGACTC CTGGGAGTGG TAG                           33

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

GGCTTCTTGA GGAGGCAGAC CAGG                                     24

(2) INFORMATION FOR SEQ ID NO:22:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

GGCTCGAGAT GGCAGACAGY GCSAAYCACC TGCC                          34

(2) INFORMATION FOR SEQ ID NO:23:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
GGCTCGAGAT GGCAGACAGY GCSAAYCACT TGCC                          34
```

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

```
ATGATGGCCT GCTCCAGAGC CTGA                                     24
```

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
ATCACCCGGG AGGAGGCWGA AGA                                      23
```

(2) INFORMATION FOR SEQ ID NO:26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

```
CCCATCGATG CCACCCAGGT AGTTGCGGCT CTG                           33
```

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

```
CTCCTGGGAG TGGTAGTGGC AGAG                                     24
```

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

```
CAATTAACCC CTCGAGAATT CCCAA                                    25
```

(2) INFORMATION FOR SEQ ID NO:29:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:29:

TCAATGAACG ATCATGTAGC AATGC                                        25

(2) INFORMATION FOR SEQ ID NO:30:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

TCAATGAACG ATCATGTAGC AATGCCAATT AACCCCTCGA GAATTCCCAA             50

(2) INFORMATION FOR SEQ ID NO:31:

(i) SEQUENCE CHARACTERISTICS:
        (A) LENGTH: 103 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

Trp Phe His Gly Lys Ile Ser Arg Glu Glu Ser Glu Gln Ile Val Leu
1               5                   10                  15

Ile Gly Ser Lys Thr Asn Gly Lys Phe Leu Ile Arg Ala Arg Asp Asn
                20                  25                  30

Asn Gly Ser Tyr Ala Leu Cys Leu Leu His Glu Gly Lys Val Leu His
            35                  40                  45

Tyr Arg Ile Asp Lys Asp Lys Thr Gly Lys Ile Ser Ile Pro Glu Gly
50                  55                  60

Lys Lys Phe Asp Thr Leu Trp Gln Leu Val Glu His Tyr Ser Tyr Lys
65                  70                  75                  80

Ala Asp Gly Leu Leu Arg Val Leu Thr Val Pro Cys Gln Lys Ile Gly
                85                  90                  95

Thr Gln Gly Asn Val Asn Phe
            100

(2) INFORMATION FOR SEQ ID NO:32:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: Synthetic DNA (xi) SEQUENCE DESCRIPTION: SEQ ID NO:32:

CGCGCGAAGC TTGGATCCTG GTTCCATGGA AAAATCTCTC GG                     42

(2) INFORMATION FOR SEQ ID NO:33:

```
    (i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Synthetic DNA (xi) SEQUENCE DESCRIPTION: SEQ ID NO:33:

GCGAATTCTC AAAAATTAAC ATTTCCCTGT GTGCC                                      35
```